(12) United States Patent
Gregory, Jr. et al.

US008236354B1

(10) Patent No.: US 8,236,354 B1
(45) Date of Patent: Aug. 7, 2012

(54) USE OF IMMUNOMODULATORS FOR THE TREATMENT OF CANCER

(75) Inventors: Daniel Tyree Gregory, Jr., Hampstead, NC (US); Stephan Dale Glenn, Weston, FL (US); Asher Nathan, Bet Shemesh (IL)

(73) Assignee: ZOR Pharmaceuticals, LLC, Wilmington, NC (US)

( * ) Notice: Subject to any disclaimer, the term of this patent is extended or adjusted under 35 U.S.C. 154(b) by 0 days.

(21) Appl. No.: 13/399,233

(22) Filed: Feb. 17, 2012

(51) Int. Cl.
*A61K 35/50* (2006.01)
*A61K 35/37* (2006.01)
*A61K 35/38* (2006.01)
*A61K 35/407* (2006.01)

(52) U.S. Cl. ......... 424/528; 424/550; 424/551; 424/553

(58) Field of Classification Search .................. 424/528, 424/550, 551, 553
See application file for complete search history.

(56) References Cited

U.S. PATENT DOCUMENTS

| 6,280,774 | B1 | 8/2001 | Rang |
| 6,551,623 | B1 | 4/2003 | Rang |
| 6,596,319 | B2 | 7/2003 | Rang et al. |
| 2004/0101511 | A1 | 5/2004 | Young |
| 2004/0101569 | A1 | 5/2004 | Rang |
| 2005/0192443 | A1 | 9/2005 | Young |
| 2006/0034938 | A1 | 2/2006 | Young |
| 2008/0279818 | A1 | 11/2008 | Young |
| 2008/0279957 | A1 | 11/2008 | Rang |
| 2011/0111047 | A1 | 5/2011 | Young |
| 2011/0158936 | A1 | 6/2011 | Wright et al. |

FOREIGN PATENT DOCUMENTS
WO 96/28175 9/1996

*Primary Examiner* — Raymond Henley, III
(74) *Attorney, Agent, or Firm* — Kohn & Associates, PLLC

(57) ABSTRACT

A method for treating a cancer, by determining a patient to have an ECOG (Eastern Cooperative Oncology Group) score of 0 or 1 and selecting that patient for treatment, and administering to the patient an effective amount of an immunomodulating composition comprising small molecular weight components of less than 3000 daltons, and having the following properties: (i) is extracted from bile of animals; (ii) is capable of stimulating monocytes and/or macrophages; (iii) is capable of modulating tumor necrosis factor production and/or release; (iv) contains no measurable level of IL-1α, IL-1β, TNF, IL-6, IL-8, IL-4, GM-CSF or IFN-γ; (v) is not cytotoxic to human peripheral blood mononuclear cells; and (vi) is not an endotoxin.

18 Claims, 14 Drawing Sheets

Survival from Study Enrollment in Months

USE OF IMMUNOMODULATORS FOR THE TREATMENT OF CANCER

BACKGROUND OF THE INVENTION

1. Technical Field

The present invention relates to methods of treating cancer. More specifically, the present invention relates to the use of an immunomodulating agent for the treatment of cancer.

2. Background Art

There are a number of therapies that are currently used in the treatment of cancer, including chemotherapeutic drugs, radiation, gene therapy, and antisense oligonucleotides. One drawback to these current therapies is the toxicity associated with most treatments, especially when such therapeutics are combined. Moreover, often large dosages must be administered over an extended period of time in order to attain therapeutic benefit. Thus, a need remains for more effective treatments that reduce the risk of toxicity and can be used in lower doses.

VIRULIZIN® (Lorus Therapeutics) is an immunotherapeutic agent that stimulates a patient's immune system to produce anti-tumor effects through several mechanisms, including the activation of macrophages including increasing TNF-α release and increasing production and secretion of IL-17E by B cells resulting in expansion in number of and increased infiltration of eosinophils and natural killer (NK) cells into tumors. The production and characterization of this bile-derived immunotherapeutic agent has been described in International Patent Application Serial No. PCT/CA94/00494, published Feb. 16, 1995 as WO 95/07089, International Patent Application Serial No. PCT/CA96/00152, published Sep. 19, 1996 as WO 96/28175, and U.S. Pat. No. 6,280,774. The use of VIRULIZIN® as an anti-viral has been described in International Patent Application Serial No. PCT/CA98/00494, published Nov. 26, 1998 as WO 98/52585.

VIRULIZIN® is comprised of small molecular weight components of less than 3000 daltons, and has one or more of the following properties: (i) is extracted from bile of animals; (ii) is capable of stimulating natural killer (NK) cells, eosinophils, monocytes and/or macrophages in vitro and/or in vivo; (iii) is capable of modulating tumor necrosis factor production and/or release; (iv) contains no measurable level of IL-1α, IL-1β, TNF, L-6, TL-8, IL-4, GM-CSF or IFN-γ; (v) shows no cytotoxicity to human peripheral blood mononuclear cells or lymphocytes; (vi) is not an endotoxin, and (vii) Inhibits growth of a variety of human tumor xenograft models in mice including melanoma, pancreatic cancer, breast cancer, ovarian cancer and prostate cancer.

Cancer clinical studies generally use performance status score as enrollment criteria, especially ECOG scale (or other methods of investigator determination of patient score, e.g. Karnofsky, WHO, Zubrod, or Lansky Scale for children). ECOG scores of either 0 and 1 or 0, 1, and 2 are generally used as selection criteria at the time of study enrollment to select patients who are capable of self-care with minimal assistance and have an higher probability of a duration of survival to allow sufficient study treatment to evaluate the safety and efficacy of the cancer treatment. No randomized placebo controlled cancer trial testing a combination of therapeutics, other than the present study has reported a highly statistically significant (p<0.001) increase in median survival observed only for the population of patients of ECOG score of 0 or 1 where the survival response (versus placebo) is specific to the treatment group receiving the test agent and there is not also at least modest increased survival versus placebo for the test agent treatment group in the ECOG score of 2 (or greater) patient population It is unexpected that only within the patient population with study enrollment ECOG score of 0 or 1 there is a highly statistically significant increase in median survival comparing the salvage treatment group treated with VIRULIZIN® (or any study drug) plus 5-FU or other chemotherapeutic and the treatment group treated with placebo plus 5-FU or other chemotherapeutic. It would be advantageous to be able to combine VIRULIZIN® with other cancer treatments in order to make these treatments more effective as well as reduce their toxicity. Furthermore, it would be advantageous to determine if VIRULIZIN is more effective for certain sets of patients than others to provide better treatment.

SUMMARY OF THE INVENTION

The present invention provides for a method for treating a cancer, by determining a patient to have an ECOG (Eastern Cooperative Oncology Group) score of 0 or 1 and selecting that patient for treatment and selecting that patient for treatment, and administering to the patient an effective amount of an immunomodulating composition comprising small molecular weight components of less than 3000 daltons, and having the following properties:
  (i) is extracted from bile of animals;
  (ii) is capable of stimulating monocytes and/or macrophages;
  (iii) is capable of modulating tumor necrosis factor production and/or release;
  (iv) contains no measurable level of IL-1α, IL-1β, TNF, IL-6, IL-8, IL-4, GM-CSF or IFN-γ,
  (v) is not cytotoxic to human peripheral blood mononuclear cells; and (vi) is not an endotoxin.

DESCRIPTION OF THE DRAWINGS

Other advantages of the present invention are readily appreciated as the same becomes better understood by reference to the following detailed description when considered in connection with the accompanying drawings wherein.

DETAILED DESCRIPTION OF THE INVENTION

Figure 1:
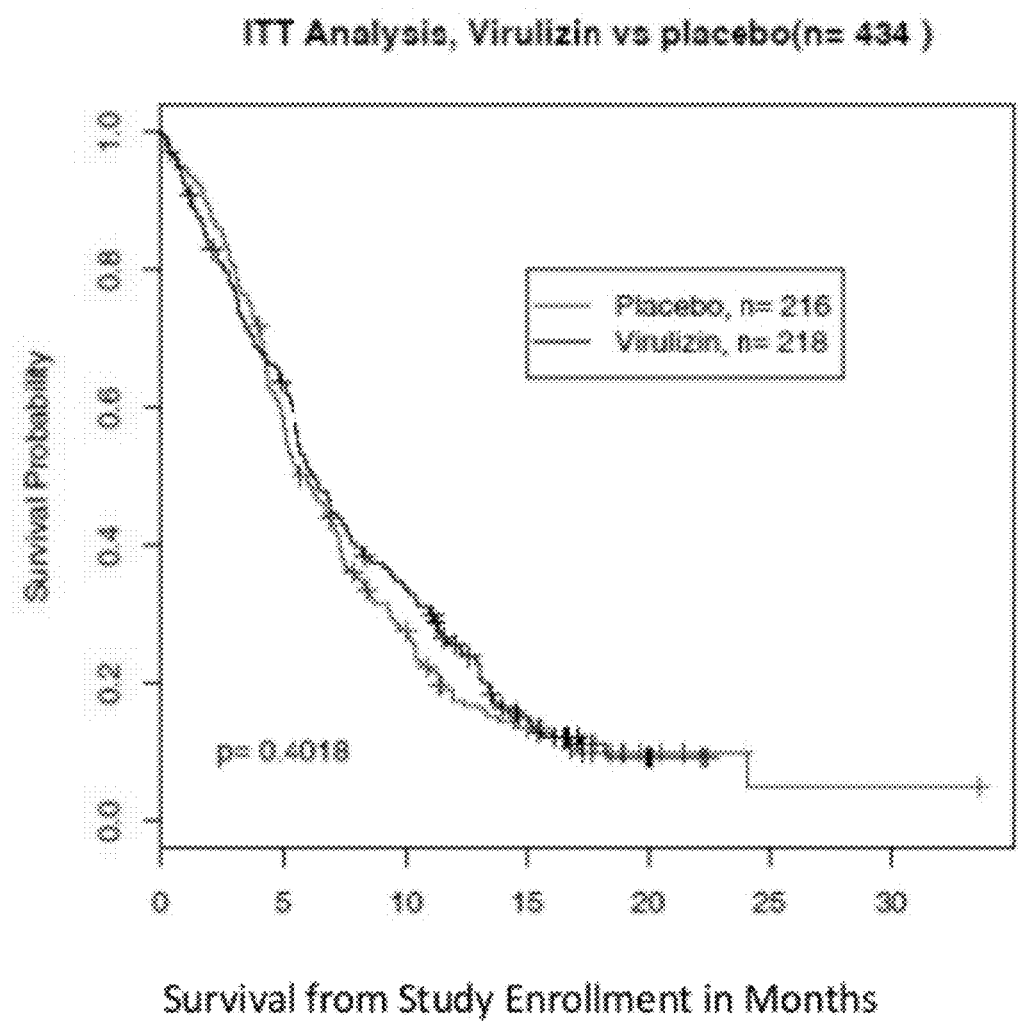
FIG. 1 is a graph summarizing the Kaplan-Meier analysis of Overall Survival of the 434 patients of the Intention to Treat population from the time of study enrollment until death from any cause or censor to follow-up.

The present invention is generally directed to methods of treating cancer and increasing survival time of cancer patients by administering an immunomodulator composition, i.e. VIRULIZIN® (Lorus Therapeutics), to a specific set of cancer patients or in combination with other cancer treatments.

As used herein, an "anticancer agent" is any compound, composition or treatment that prevents or delays the growth and/or metastasis of cancer cells.

As used herein, "cancer" refers to all types of cancer or neoplasm or malignant tumors found in mammals, including carcinomas and sarcomas. Examples of cancers are cancer of the brain, breast, cervix, colon, head and neck, kidney, lung, non-small cell lung, melanoma, mesothelioma, ovary, pancreas, sarcoma, stomach, uterus and medulloblastoma.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease—acute or chronic; (2) the type of cell involved; myeloid (myelogenous), lymphoid (lymphogenous), or monocytic; and (3) the increase or non-increase in the number of abnormal cells in the blood—leukemic or aleukemic (subleukemic). Leukemia includes, for example, acute nonlymphocytic leukemia, chronic lymphocytic leukemia, acute granulocytic leukemia, chronic granulocytic leukemia, acute promyclocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyclocytic leukemia, Rieder cell leukemia, Schilling's leukemia, stem cell leukemia, subleukemic leukemia, and undifferentiated cell leukemia.

The term "sarcoma" generally refers to a tumor which is made up of a substance like the embryonic connective tissue and is generally composed of closely packed cells embedded in a fibrillar or homogeneous substance. Sarcomas include chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, amyeloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocytic system of the skin and other organs. Melanomas include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, and superficial spreading melanoma.

The term "carcinoma" refers to a malignant new growth made up of epithelial cells tending to infiltrate the surrounding tissues and give rise to metastases. Exemplary carcinomas include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epidermoid carcinoma, carcinoma epithelioma adenoides cysticum, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, naspharyngeal carcinoma, oat cell carcinoma, carcinoma ossificans, osteoid carcinoma, pancreatic adenocarcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

Additional cancers include, for example, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulinoma, malignant carcinoid, urinary bladder cancer, pre-malignant skin lesions, testicular cancer, lymphomas, thyroid cancer, neuroblastoma, esophageal cancer, genitourinary tract cancer, malignant hypercalcemia, cervical cancer, endometrial cancer, adrenal cortical cancer, and prostate cancer.

As used herein, a "dosage unit" is a pharmaceutical composition or formulation comprising at least one active ingredient and optionally one or more inactive ingredient(s). The dosage unit can be unitary, such as a single pill or liquid, containing all of the desired active ingredients and the inactive ingredients necessary and desired for making a dosage suitable for administration (e.g., tabletting compounds such as binders, fillers, and the like); the dosage unit can consist of a number of different dosage forms (e.g., pill(s) and/or liquid(s)) designed to be taken simultaneously as a dosage unit.

The immunomodulating composition used in the present invention (VIRULIZIN®) can be prepared and characterized as described in International Patent Application Serial No. PCT/CA94/00494, published Feb. 16, 1995 as WO 95/07089. Briefly, the immunomodulating composition used in the present invention is prepared by (a) mixing bile from an animal, preferably a bovine, with a solvent that is soluble or miscible with water, preferably an alcohol, and preferably with an equal volume of an alcohol, to produce a bile/alcohol solution; (b) separating the solution which preferably is an alcohol soluble fraction, and isolating therefrom a solution substantially free of alcohol, as by removing most of the alcohol, such as by the use of heat; (c) removing bile pigments from the solution preferably using activated charcoal to obtain a colorless liquid; (d) optionally treating the colorless liquid to substantially remove any residual alcohol; (e) removing fatty organic materials, as by extracting the colorless liquid with an ether and isolating the aqueous phase; (f) optionally removing residual ether from the aqueous phase; and (g) sterilization by microfiltration and (h) cycles of Tyndalization.

Compounds likely to be present in the present composition, considering the source, include sulfonated bile acids, oxidized bile acids, other naturally occurring bile acids, and their amino acid (especially glycine and taurine) conjugates and sterols. Accordingly, it is believed that the present composition includes at least one compound having the formula

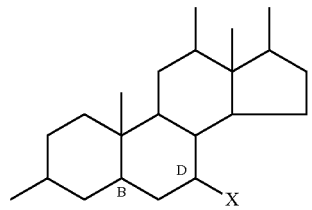

wherein the molecule may or may not be fully saturated, such that, for example, the bond between A and B, B and C, or C and D may be single or double bonds, and wherein X is H, OH, =O, or OSO3H; and Y is

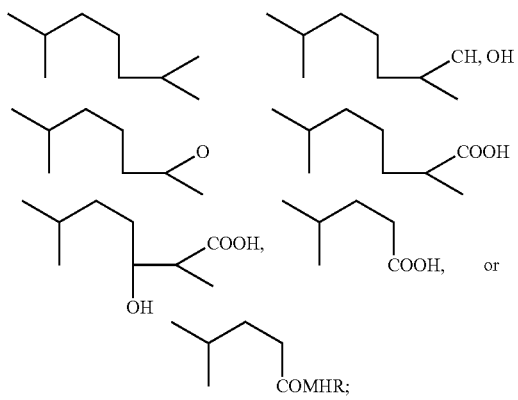

and wherein R is an amino acid residue, such as, for example, glycyl, glutamyl, or tauryl, thereby forming the glycine, glutamyl, or taurine conjugate.

In particular, the composition of the present invention has been analyzed as to its component compounds, including organic and inorganic components. Such information was derived using standard methods of analytical chemistry, including mass spectroscopy (MS). The results of such studies include, for example, the identification of specific bile acid compounds thought to be present, including cholic acid, glycocholic acid, deoxyglycocholic acid, ursodeoxycholic acid, cholesterol sulfate, deoxycholic acid, chenodeoxycholic acid, and taurocholic acid.

From the MS analysis it is not distinguishable if the loss of OH and H2 of some compounds are occurring in the MS analysis or if the deoxy, dideoxy and unsaturated analogs of such compounds are also present to begin with. These compounds may all be present as salts of ammonium, alkylammonium and inorganic cations.

The MS analysis also supports the identification in the present composition of phospholipids, sphingolipids and related agents capable of forming miscelles. Specific compounds thought to be present include: stearic acid CH3(CH2)16COOH, palmitic acid CH3(CH2)14COOH, oleic acid Z-9, octadecanoic acid CH3(CH2)2CH2CH=CHCH2(CH2)6COOH oxidized or hydroxylated/unsaturated short chain fatty acids: C6H8O3 (e.g., CH3CH=CHCOCH2COOH or a C6 acid with 2 double bonds and a hydroxide), acetic acid stearic acid diglyceride, palmitic acid diglyceride, stearic acid, palmitic acid diglyceride, stearic acid-monoglyceride-phosphocholine (a lysolecithin), stearic acid monoglyceride, stearic acid triglyceride, palmitic acid monoglyceride, phosphocholine, phosphoserine, phosphosphingosine, sphingomyelin, phosphoglycerol, glycerol, stearic acid-sphingosine, sphingosine, stearic acid amide, stearic acid methylamide choline, glycerophosphocholine, stearic acid, oleic acid diglyceride, stearic acid, oleic acid phosphoglycerol, palmitic acid amide, lecithin sialic acid-glycerol dimer.

In addition, preliminary HPLC and titration evidence has been obtained which shows that shorter chain fatty acids are also present, such as those having from 1 to about 30 carbon atoms.

Phospholipid, sphingolipid, and related hydrolysis product compounds likely to be present considering the source and the information derived from the MS and High Performance Liquid Chromatography analyses include at least one compound having the formula

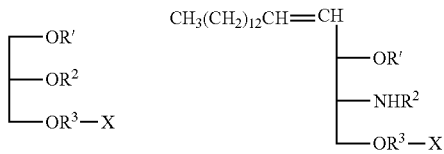

where R', R2, R3 are different or the same and are H, COR4, CH=CH—R5, X, —P(O)(OH)O—, or —S(O)2O—; X is selected from the group consisting of choline, ethanol amine, N-alkylated ethanolamines, serine, inositol, sugars bearing free hydroxyls, amino-sugars, sulfonated sugars, and sialic acids; R4 is C1-C30 alkyl that is saturated or unsaturated, oxidized or hydroxylated; and R5 is an alkyl group or oxidized and/or hydroxylated analogs thereof.

The fatty acids and their conjugates can be present in the aforementioned aqueous extract as salts.

The solubility of such compounds is also enhanced by other components of the mixture. Amides of the included carboxylic acids, RCONR'R2, where R' and R2 are the same or different and are H or alkyl, are also believed to be present.

A third class of compounds, namely, mucin and proteoglycan hydrolysis products and metabolites, are also likely to be present, considering the source of the composition and the aforementioned MS analysis thereof.

Such compounds include hydrolysis products of mucoproteins from bile and from the gallbladder wall, such as: chondroitin 4- and 6-sulfates, dermatan sulfate, heparin, heparin sulfate, hyaluronic acid and the hydrolysis products (monomers, dimers, oligomers and polymers) of these mucins. Mucins and proteoglycans can be hydrolyzed, which hydrolysis products would include: N-acetyl-D-galactosamine-4-sulfate, galactose-6-sulfate, N-acetyl-D-glucosamine-6-sulfate, glucosamine-6-sulfate, D-glucosamine 2-sulfate, D-glucosamine 2,3-disulfate, D-galactose-6-sulfate, glucuronic acid 2-sulfate, N-acetylneuraminic acid, sialic acid, N-acetyl chondrosine, chondroitin 4-sulfate, chondroitin 6-sulfate, D-glucosamine, D-galactosamine, glucuronic acid, glucose, galactose, mannose, fucose, iduronic acid, hexose, hexosamine, ester sulfate, glucuronic acid, chondrosamine, 2-amino-2-deoxy-D-galactose, serine, proline, threonine, alanine glycine taurine, glutamic acid, aspartic acid, histidine, and small peptides.

Similar products would be obtained by hydrolysis of mucins such as keratin sulfates, dermatan sulfates the natural sugar-sugar linkages in the dimers, oligomers and polymers may be replaced by —O—Si(OH)2-O— bridges between the sugar monomers or adjacent sugar chains.

In particular, specific mucin and proteoglycan hydrolysis product compounds thought to be present include: sialic acids and their mono and diacetylated and glycolylated monomers; N-acetylneuraminic acid; hexosamines, such as glucosamine; L-fucose; hexosamine-hexuronic acid (dimer) disulfate; glucuronic acid; glucuronic acid or iduronic acid sulfate, monoacetylated; sialic acid-glycerol (dimer); and dimers, trimers, oligomers & polymers of the above monomers in acetylated & sulfated form.

A fourth class of compounds, namely fat-soluble vitamins, likely to be present considering the source and the aforementioned MS analysis, include Vitamins A, D, and K (e.g. A2, D1, D3, D4, K1, K2, K5, K6, K7, K-S(II), and Vitamin E acetate).

In particular, specific fat-soluble vitamin compounds thought to be present include at least one of the group consisting of Vitamin A2, Vitamin D1, Lumisterol (present from its vitamin D1 complex), Vitamin E, Vitamin K1 oxide, and Vitamin K5.

Various miscellaneous organic compounds are likely to be present, considering the source and the aforementioned MS analysis. Such compounds include: urea; alkylamines, including methylamine, dimethylamine, ethylamine, methylethylamine, diethylamine, dipropylamine, and/or butylethylamine; amino acids, including taurine, glutamic acid, glycine, alanine, leucine, norleucine, phosphoserine, phosphoethanolamine, aspartic acid, threonine, serine, sarcosine, □-amino adipic acid, citrulline, valine, isoleucine, □-alanine, □-amino butyric acid (GABA), hydroxylysine, ornithine, and lysine; bilirubin and its gluconuride conjugate; biliverdin and its gluconuride conjugate; butylated hydroxytoluene (BHT); polyethylene glycol (PEG); traces of steroids and metabolites thereof; other plasma solutes, such as sugars, purines and pyrimidines; miscellaneous dietary lipids; and glutathione and its hydrolysis products. In particular, specific miscellaneous organic compounds believed to be present in the composition include at least one of the group consisting of urea, methyl amine, dimethylamine, ethylamine, methylethylamine, diethylamine, dipropylamine, butylethylamine, ammonia, choline, taurine, glutamic acid, glycine, alanine, phosphoserine, phospho-ethanolamine, aspartate, threonine, serine, sarcosine, □-amino butyric acid, citrulline, valine, isoleucine, leucine, □-alanine, □-aminobutyric acid (GABA), hydroxylysine, ornithine, lysine, butylated hydroxytoluene (BHT), and polyethylene glycol (PEG).

Amines present in the present composition, particularly the secondary amines, may include nitrogen oxides from the air, thus forming nitroso compounds. N-oxides and N-carbamate byproducts may also be included. This series of amines cited above should be extended to include all primary, secondary and tertiary alkylamines.

Certain inorganic elements have been identified and quantified (mg/l) in the immunomodulating composition as follows: Tungsten 0.07, Zinc 0.666, Phosphorus 378, Cadmium 0.01, Cobalt 0.008, Nickel 0.022, Barium 0.032, Iron 0.022, Manganese 0.039, Chromium 0.060, Magnesium 7.46, Aluminum 0.136, Calcium 5.97, Copper 0.087, Titanium 0.01, Strontium 0.060, Sodium 9600, Potassium 483, Chloride 15400, Ammonia 218, and Vanadium 1 parts per million (ppm).

The immunomodulating composition has a consistently reproducible pattern on reverse-phase HPLC. The composition can be used in a concentrated form. The composition can also be lyophilized. The composition can be used without further modification by sterile filtration, aseptic packaging it in vials and cycles of Tindallization to accomplish sterilization.

More specifically, the present invention provides for a method of treating cancer, by determining a patient to have an ECOG (Eastern Cooperative Oncology Group) score of 0 or 1 and selecting that patient for treatment, and administering to the patient an effective amount of an immunomodulating composition comprising small molecular weight components of less than 3000 daltons, and having the following properties: (i) is extracted from bile of animals; (ii) is capable of stimulating natural killer (NK) cells, eosinophils, monocytes and/or macrophages; (iii) is capable of modulating tumor necrosis factor production and/or release; (iv) contains no measurable level of IL-1α, IL-1β, TNF, IL-6, IL-8, IL-4, GM-CSF or IFN-γ; (v) is not cytotoxic to human peripheral blood mononuclear cells; and (vi) is not an endotoxin.

The Eastern Cooperative Oncology Group (ECOG) scale is a set of criteria used by doctors and researchers to assess how a patient's disease is progressing, assess how the disease affects the daily living abilities of the patient, and determine appropriate treatment and prognosis. The WHO and Zubrod scales are the same as the ECOG scale. See Oken, M. M., Creech, R. H., Tormey, D. C., Horton, J., Davis, T. E., McFadden, E. T., Carbone, P. P.: Toxicity And Response Criteria Of The Eastern Cooperative Oncology Group. Am J Clin Oncol 5:649-655, 1982. Table 1 sets forth the assessment criteria and the corresponding ECOG score, which varies from 0 to 5. A physician or medical practitioner can readily determine the ECOG score of a patient to determine if the composition of the present invention should be administered, i.e. a score of 0 or 1. As demonstrated in the Examples below, a patient with an ECOG score of 0 or 1 is more likely to respond with increased to treatment with the immunomodulating composition resulting in increased survival versus the patients with an ECOG score of 2 or greater. Therefore, the composition and combinations with other anticancer treatments can be tailored to this particular group of patients for a personalized medicine approach.

TABLE 1

| Score | Assessment Criteria |
|---|---|
| 0 | Fully active, able to carry on all pre-disease performance without restriction. |
| 1 | Restricted in physically strenuous activity but ambulatory and able to carry out work of a light or sedentary nature, e.g., light house work, office work. |

TABLE 1-continued

| Score | Assessment Criteria |
|---|---|
| 2 | Ambulatory and capable of all self care but unable to carry out any work activities. Up and about more than 50% of waking hours. |
| 3 | Capable of only limited self care, confined to bed or chair more than 50% of waking hours. |
| 4 | Completely disabled. Cannot carry on any self care. Totally confined to bed or chair. |
| 5 | Dead. |

The administration of the immunomodulating composition can be by injection. Preferably, intramuscular injections are given three times weekly of 3 mL. VIRULIZIN® activity is determined in a validated in vitro bioassay. One (1) Unit of VIRULIZIN® is defined as the quantity to increase the release of 1 pg Tumor Necrosis Factor alpha (TNF□) under standardized conditions in 1 mL of cell culture medium containing lipopolysacharide (LPS) primed human U-937 cells. In general, a dosage range of the composition is envisaged for administration in human medicine of from about 723 to 144,600 Units, preferably from about 7230 to 72,300 Units, most preferably 7,230 to 36,150 Units per dose administered 3 times per week (e.g. Monday, Wednesday, and Friday), can be employed. In the case of intravenous administration, the dosage is about 7,230 to 72,300 Units per dose administered 3 times per week (e.g. Monday, Wednesday, and Friday), and in the case of oral administration the dosage is about 14,460 to 144,600 Units per dose administered 3 times per week (e.g. Monday, Wednesday, and Friday.) Where a concentrated composition is used, approximately half the above-mentioned dosages can be used. For example, for intramuscular administration, a dosage of about 7,230 to 72,300 Units per dose administered 3 times per week (e.g. Monday, Wednesday, and Friday), preferably 7,230 to 72,300 Units per dose administered 3 times per week (e.g. Monday, Wednesday, and Friday) may be used. The present schedule of 3 times weekly is maintained for as long as tolerated and medically indicated, preferably, up to 24 months. A number of patients have received VIRULIZIN® for 1 year or longer. Alternative administration procedures are further described below. Preferably, the immunomodulating composition is in a pharmaceutically acceptable carrier.

The mechanism of action of the immunomodulating composition is as follows. Most generally, the immunomodulating composition activates macrophages and monocytes and subsequently enhances cell-mediated immune response to tumors. The immunomodulating composition can stimulate normal peripheral blood monocytes (PBMNs) and regional, tumor-associated macrophages to express cytocidal activity through the increased expression of TNF-α, and can stimulate macrophages in cancer patients that are unresponsive to stimulation by conventional activators. The immunomodulating composition is insensitive to inhibitory effects of prostaglandins. The composition enhances cell-mediated immune response by increasing production and secretion of IL-17E by B cells resulting in expansion in number of and increased infiltration of eosinophils and natural killer (NK) cells into tumors.

Preferably, the cancer that is treated according to the present invention is pancreatic cancer, malignant melanoma, breast cancer, prostate cancer, ovarian cancer, endometrial cancer, lung cancer, Kaposi's sarcoma, leukemia, lymphoma, gastric cancer, colon cancer, colorectal cancer, esophageal cancer, renal cancer, or head and neck cancer. The method can also be used for pancreatic cancer that is gemcitabine resistant. However, any other cancer as described above can also be treated.

The method can further include administering an effective amount of at least one anticancer agent to the individual. The anticancer agent(s) and the immunomodulator composition can be administered simultaneously or administered independently in a fashion such that the components act at the same time. Components administered independently can, for example, be administered separately (in time) or concurrently at different sites of administration or via different routes of administration. Separately in time means at least minutes apart, and potentially hours, days or weeks apart. In the case of separate administration, the immunomodulator composition can be administered before, during or after administration of the anticancer agent(s) at different sites or via different routes of administration. A worker skilled in the art can determine the elapsed time between the administration of the components of the invention when used in combination will be dependent upon, for example, the age, health, and weight of the recipient, nature of the combination treatment, side effects associated with the administration of other component(s) of the combination, frequency of administration(s), and the nature of the effect desired. Components of the combinations of the invention can also be administered independently with respect to location and, where applicable, route of administration in order to maximize the therapeutic benefit of each component. The immunomodulator composition and/or the anticancer agent(s) of the combination can be administered via a single dose or via continuous perfusion In previous studies of the immunomodulator composition, treatment schedules have included loading doses of VIRULIZIN® administered daily for 15, 21, 30, or 60 days. In some studies these daily loading dose schedules were followed by schedules of 3 doses per week or doses administered every 2 days, then every 3 days, then every 4 days, then 5 days for periods of 45 to 313 days. Other studies included schedules of 3 doses per week for as long as clinically indicated.

The preferred dosing schedule of 3 times per week (Monday, Wednesday, and Friday) was used in the Phase 3 pancreatic cancer trial. A total of 217 Stage 1 or 2 patients in the VIRULIZIN® plus gemcitabine group were administered a mean (SE) of 50.8 (2.93) doses by intramuscular injection. In addition, a total of 76 of the patients who continued on Stage 3 of this trial received VIRULIZIN® administered as a mean (SE) of 56.5 (6.14) additional doses.

Such anticancer agents include, but are not limited to, chemotherapeutic drug treatment, radiation, gene therapy, hormonal manipulation, immunotherapy and antisense oligonucleotide therapy. Anticancer agents for use in this invention also include novel compounds or treatments developed in the future that can be used to generate therapeutic combinations as described herein.

Examples of anticancer agents that can be used in the methods of the present invention are: antisense sequences, Drugs for Promyelocytic Leukemia: Tretinoin (VESANOID® (Roche)); Drugs for Chronic Myeloid Leukemia: Low-dose Interferon (IFN-α); Drugs Used in Gastric Cancer: Antibiotics, Antineoplastics; Acute Lymphoblastic Leukemia: Pegaspargase (ONCASPAR® (Sigma-Tau Pharmaceuticals, Inc.)), L-asparaginase, Il-2; Drugs for Colon Cancer: Edatrexate or 10-ethyl-10-deaza-aminopterin or 10-edam, 5-fluorouracil (5-FU) and Levamisole, Methyl-ccnu (Methyl-chloroethyl-cyclohexyl-nitrosourea), Fluorodeoxyuridine (Fudr), Vincristine; Drugs for Esophageal Cancer: Porfimer Sodium (PHOTOFRIN® (Pinnacle Biologics, Inc.)), or Treatment with a Neodymium:yag (Nd:YAG) Laser; Drugs Used in Colorectal Cancer Irinotecan (CAMPTOSAR® (Pfizer, Inc.)), Topotecan (HYCAMTIN® (GlaxoSmithKline)), Loperamide (IMODIUM® (McNeil, PPC)), 5-fluorouracil (5-FU); Drugs For Advanced Head and Neck Cancers: Docetaxel (TAXOTERE® (Sanofi Aventis)); Drugs for Non-Hodgkin's Lymphoma: Rituximab, Etoposide; Drugs for Non-small-cell lung Cancer: A Vinca Alkaloid, Vinorelbine Tartrate (NAVELBINE® (GlaxoSmithKline)), Paclitaxel (TAXOL® (Bristol-Myers Squibb)), ABRAXANE® (Paclitaxel, (Celgene)), Docetaxel (TAXOTERE® (Sanofi Aventis)), Topotecan, Irinotecan, Gemcitabine; Drugs for Ovarian Cancer: Docetaxel (TAXOTERE® (Sanofi Aventis)), Gemcitabine, (GEMZAR® (Eli Lilly and Company)), Irinotecan (CAMPTOSAR® (Pfizer, Inc.)), Paclitaxel (TAXOL® (Bristol-Myers Squibb)), Doxil (liposomal doxorubicin), Topotecan (HYCAMTIN® (GlaxoSmithKline)), Amifostine (ETHYOL® (MedImmune)); Drugs to treat unresectable Melanoma: Roche, Temozolomide (TEMODAR® (Merck)), Dacarbazine (DTIC), and Interferon Alfa-2b; Drugs for Prostate Cancer Flutamide (EULEXIN® (Schering-Plough)), Finasteride (PROSCAR® (Merck)), Terazosin (HYTRIN® (Abbott)), Doxazosin (CARDURA® (Pfizer)), Goserelin Acetate (ZOLADEX® (AstraZenica)), Liarozole, Nilutamide (NILANDRON® (Sanofi Aventis)), Mitoxantrone (NOVANTRONE® (OSI Pharmaceuticals)), Prednisone (DELTASONE® (Space Age Holdings)); Drugs for Pancreatic Cancer: Gemcitabine (GEMZAR® (Eli Lilly and Company)), 5-fluorouracil, (Adrucil, FLUDARA® (Genzyme)), capecitabine (Xeloda), tegafur (UFT, UFUR, Uracil); Drugs for Advanced Renal Cancer: Interleukin-2 (PROLEUKIN® (Prometheus Laboratories, Inc.)); Additional Anti-neoplastic Drugs: Porfimer Sodium, Dacarbazine, Etoposide, Procarbazine HCl, Rituximab, Paclitaxel (TAXOL® (Bristol-Myers Squibb)), Trastuzumab (HERCEPTIN® (Roche)), Temozolomide (TELMODAL® (Schering-Plough)); Alkylating Agents Used in Combination Therapy for Different Cancers Cyclophosphamide, Cisplatin, Melphalan.

Examples of antisense compounds useful in the methods of the present invention include oligonucleotides containing modified backbones or non-natural internucleoside linkages. In accordance with the present invention, oligonucleotides having modified backbones include those that retain a phosphorus atom in the backbone and those that do not have a phosphorus atom in the backbone. For the purposes of the present invention, and as sometimes referenced in the art, modified oligonucleotides that do not have a phosphorus atom in their internucleoside backbone can also be considered to be oligonucleosides.

The antisense compounds used in accordance with this invention can be conveniently and routinely made through the well-known technique of solid phase synthesis. Equipment for such synthesis is sold by several vendors including, for example, Applied Biosystems (Foster City, Calif.). Any other means for such synthesis known in the art may be additionally or alternatively employed. Similar techniques using phosphorothioates and alkylated derivatives have been employed to produce oligonucleotides.

Antisense oligonucleotides have been successfully employed as therapeutic moieties in the treatment of disease states such as cancer. Antisense compounds exert their effects by specifically modulating expression of a gene implicated in a specific disease state. Thus, the present invention contemplates the therapeutic administration of an effective amount of a combination of the immunomodulator composition of the present invention and an appropriate antisense compound to a mammal suspected of having a disease or disorder, which can be treated by specifically modulating gene expression. The present invention further contemplates the prophylactic use of a combination of the immunomodulator composition and an antisense compound in the prevention of a cancer, which is related to over- or under-expression of a specific gene.

More preferably, in the methods of the present invention, the anticancer agent is a chemotherapeutic drug such as gemcitabine, 5-fluorouracil, dacarbazine, taxol, taxotere, cisplatin, irinotecan, or mitoxantrone. If the cancer (e.g., pancreatic cancer) is gemcitabine resistant, the chemotherapeutic agent is preferably 5-fluorouracil (5-FU), folinic acid, oxaliplatin, capecitabine, erlotinib, dacarbazine, taxol, taxotere, cisplatin, irinotecan, mitoxantrone, or combination therapies including one or more of these agents including gemcitabine. For example, gemcitabine can be administered 1 g/m2 weekly for the first 7 weeks of treatment, followed by a week of rest, and then 28-day cycles with gemcitabine dosing on days 1, 8 and 15. 5-FU can be administered by intravenous infusion at a dose of 600 mg/m2 weekly with dose adjustments as per the product insert if needed as a result of toxicity. Alternatively, 5-FU can be administered on a dosing regimen of 12 mg/kg given intravenously once daily for 4 successive days. Furthermore, 5-FU can be administered intravenously in a dose of 300 to 2400 mg/m2 weekly or capecitabine administered orally at a dose of 2500 mg/m2 daily with food for 2 weeks followed by a 1-week rest period given as 3 week cycles. The daily dose should not exceed 800 mg. If no toxicity is observed, 6 mg/kg are given on the 6th, 8th, 10th, and 12th days unless toxicity occurs. No therapy is given on the 5th, 7th, 9th, or 11th days. Therapy is to be discontinued at the end of the 12th day, even if no toxicity has become apparent. Poor risk patients or those who are not in an adequate nutritional state should receive 6 mg/kg/day for 3 days. If no toxicity is observed, 3 mg/kg can be given on the 5th, 7th, and 9th days unless toxicity occurs. No therapy is given on the 4th, 6th, or 8th days. The daily dose of 5-FU should not exceed 400 mg. A sequence of injections on either schedule constitutes a "course of therapy." In instances where toxicity has not been a problem, it is recommended that therapy be continued using either of the following schedules:

1. Repeat dosage of first course every 30 days after the last day of the previous course of treatment.

2. When toxic signs resulting from the initial course of therapy have subsided, administer a maintenance dosage of 10 to 15 mg/kg/week as a single dose. Do not exceed 1 gm of 5-FU per week.

Preferably, gemcitabine is administered during administration of the immunomodulating composition, and subsequently 5-fluorouracil is administered during administration of the immunomodulating composition as further described in Example 1. Any of the anticancer agents described herein can be formulated for intravenous administration or oral administration where appropriate, or any other administration method as described below.

Other compositions can also be administered before, during, or after administration of the immunomodulating composition and anticancer agent. For example, drugs to treat adverse side effects of the cancer and anticancer agents can be administered concurrently with the compositions of the present invention. During the conduct of the Phase 3 trial of VIRULIZIN® versus placebo in 434 patients with advanced pancreatic cancer, the use of concomitant medication(s) was reported by 417 (96.8%) patients in the safety analysis set. The concomitant medications [indicated use, percent of patients reporting] included: serotonin (5ht3) antagonists [depression, 205 patients, 47.6%], natural opium alkaloids [pain, 197 patients, 45.7%], propulsives [constipation, 141 patients, 32.7%], glucocorticoids [anti-inflammatory, 138 patients, 32.0%], pyrazolones [anti-inflammatory, 131 patients, 30.4%], benzodiazepine derivatives [anxiety, 130 patients, 30.2%], enzyme preparations [insufficiency of pancreatic digestive enzymes, 125 patients, 29.0%], anilides [anti-inflammatory, 122 patients, 28.3%], other opioids [pain, 120 patients, 27.8%], proton pump inhibitors [control acid-peptic disorders, 112 patients, 26.0%], sulfonamides, plain [infection/anti-bacterial, 110 patients, 25.5%], and aminoalkyl ethers [respiratory anti-inflammatory/antihistamine, 106 patients, 24.6%].

ECOG score determined at study enrollment or treatment initiation has been reported as a potential prognostic of patient survival in numerous cancer clinical studies and ECOG score to specifically be useful for predicting the outcome of clinically important endpoints such as median survival or progression free survival in cancer patients. It is generally reported that the survival of patients with ECOG score of 0 or 1 is greater than the survival of patients with ECOG score of 2 or greater whether the patients are treated with best supportive care or effective cancer therapy (surgery, chemotherapy, or radiotherapy.) The 2011 publication of a single-arm treatment clinical trial (Martinez-Salamanca J I, et al.) reports the highly statistically significant prognostic role of lower ECOG score (e.g. ECOG score of 0 or 1) as an independent predictor of Overall Survival ($p<0.001$) for patients with urothelial carcinoma compared to the population of patients with higher ECOG score (e.g. ECOG score of 2).

Another 2011 publication (Chibaudel B., et al) reports on a clinical study that was aimed at developing a prognostic model for patients with previously untreated metastatic colorectal cancer. Treatment in this study was either oxaliplatin-based or irinotecan-based first-line chemotherapy. Three Independent prognostic factors were identified: (WHO score ($p<0.001$), serum lactate dehydrogenase (LDH) ($p<0.001$), and number of metastatic sites ($p=0.005$) by using multivariate analysis with overall survival as the efficacy endpoint.

A 2011 publication (Lim K H, et al.) of a single-arm clinical study of salvage treatment of patients with pancreatic cancer that had recurred after gemcitabine treatment reports the results of a combination treatment consisting of infusional 5-fluorouracil, doxorubicin, and mitomycin-C. The investigators analyzed potential prognostic factors including ECOG scores of 0 to 2 at study enrollment. The analysis concluded that determining ECOG score at study enrollment is a significant prognostic factor for Overall Survival ($P=0.022$) and that the combination therapy of infusional 5-fluorouracil, doxorubicin, and mitomycin-C is effective and well-tolerated in patients with pancreatic cancer that has been previously treated gemcitabine, including patients with ECOG score of 2.

A 2009 publication (Furuse, J., et al.) reports analysis of a single-arm phase II study of uracil-tegafur plus doxorubicin to treat patients with unresectable biliary tract cancer for prognostic factors using multivariate analysis of factors potentially related to median Overall Survival. This analysis found that ECOG score has the greatest prognostic value of the factors analyzed in this clinical study with a p value of 0.001).

Yet another 2011 publication (Vickers, M M, et al.) reports the results of a randomized placebo controlled combination chemotherapy (gemcitabine plus erlotinib versus gemcitabine plus placebo) clinical trial in patients with advanced pancreatic cancer. Included in the statistical analysis is an examination of the potential of multiple factors to predict survival. This study reports that of the factors examined, only two were prognostic of survival: ECOG score and baseline pain intensity. Low ECOG score of 0 or 1 at study enrollment correlated very highly with greater overall survival for both treatment arms when compared to the study population with High ECOG score of 2 at study enrollment (p value less than 0.0001). The investigators also report that High ECOG score of 2 (with p value of 0.02), but not Low ECOG score of 0 or 1 is prognostic of increased Overall Survival in patients treated with gemcitabine plus erlotinib versus survival of patients treated with gemcitabine plus placebo.

Although numerous studies in a variety of cancers report that Low ECOG score of 0 or 1 at study enrollment is the strongest predictor of greater survival, Low ECOG score of 0 or 1 has not been reported in the medical literature as a prognostic of greater survival related for one treatment regimen versus another in comparative treatment trials.

Performance status score has not been reported to be of prognostic value for predicting response to one treatment versus another in any cancer clinical study, except for survival of patients of Low ECOG of 0 or 1 treated with VIRULIZIN® plus 5-FU versus placebo plus 5-FU in study Stage 3 of the present study. The patients in this study were not surgically resectable and were treated with the only standard first-line therapy for advanced pancreatic cancer (gemcitabine). Stage 3 of the present study represents salvage therapy for advanced pancreatic cancer, since 5-FU is the only other approved chemotherapy agent for salvage treatment of pancreatic cancer for patients who have failed gemcitabine. Preferably, the present invention is used to treat patients who have previously been administered gemcitabine and failed gemcitabine therapy. Also, the present invention can be used to treat patients that have cancer that has recurred or advanced after previous radiotherapy, surgical resection, or chemotherapy.

Because the immunostimulatory mechanism of action of VIRULIZIN® anticancer activity (proliferation, activation and tumor infiltration of macrophages and monocytes with anticancer activity) likely requires prolonged and repeated dosing with this immunomodulator agent. ECOG score is likely prognostic of increased patient survival. Thus, selection of a patient population with Low ECOG score of ECOG=0 or 1 for treatment with an immunomodulator agent and the minimal side effects associated with the immunomodulator agent increases the immunotherapy treatment window with said immunomodulator agent. Selecting a patient with Low ECOG score and the resulting increased treatment window improves the likelihood of therapeutic benefit. Patients with an ECOG score of 0 or 1 who receive further chemotherapy (in combination with the immunomodulator agent) are more likely to tolerate chemotherapy for more cycles at full dose and with fewer side effects than patients with an ECOG score of 2 or higher. Combined these factors increase the immunomodulator treatment window increasing the probability of anticancer benefit and increased survival for the ECOG score 0 or 1 patient population. Patients with a worse prognosis (baseline ECOG score of 2 or greater at study entry) would be more likely to have a shorter progression free or disease free intervals and resulting in a shorter potential immunotherapeutic window. Combining an immunomodulator agent with a chemotherapeutic agent increased median survival apparently by the chemotherapy slowing cancer progression and allowing an increased and more effective immunotherapeutic window. This appears to be a general concept, unless the chemotherapeutic agent interferes with the anticancer immunostimulatory activity of the immunomodulator agent or specifically inhibiting the cellular immune response.

The primary study endpoint was survival from study enrollment until death from any cause or censor to follow-up had no statistically significant (p=0.4018) increase in median survival of patients treated with gemcitabine plus VIRULIZIN® versus patients treated with placebo (see FIG. 1.)

The present invention also provides for a method of increasing the survival rate of a cancer patient, by determining a patient to have an ECOG (Eastern Cooperative Oncology Group) score of 0 or 1 and selecting that patient for treatment, administering to the patient an effective amount of an immunomodulating composition comprising small molecular weight components of less than 3000 daltons, and having the following properties: (i) is extracted from bile of animals; (ii) is capable of stimulating natural killer (NK) cells, eosinophils, monocytes and/or macrophages; (iii) is capable of modulating tumor necrosis factor production and/or release; (iv) contains no measurable level of IL-1α, IL-1β, TNF, IL-6, IL-8, IL-4, GM-CSF or IFN-gamma; (v) is not cytotoxic to human peripheral blood mononuclear cells; and (vi) is not an endotoxin, and increasing the survival rate of the cancer patient.

Each of these steps can be performed as described above. One advantage of the present invention is that it can increase the survival rate of cancer patients, and prolong their lifetime. Preferably, the method prolongs lifetime by at least 6 weeks, at least 13 weeks, or at least 26 weeks.

The compound of the present invention is administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement including but not limited to improved survival rate or more rapid recovery, or improvement or elimination of symptoms and other indicators as are selected as appropriate measures by those skilled in the art.

In the method of the present invention, the compound of the present invention can be administered in various ways. It should be noted that it can be administered as the compound and can be administered alone or as an active ingredient in combination with pharmaceutically acceptable carriers, diluents, adjuvants and vehicles. The compounds can be administered orally, topically, rectally, locally, by inhalant, intracerebrally, subcutaneously or parenterally including intravenous, intraarterial, intramuscular, intraperitoneally, intratonsillar, and intranasal administration as well as intrathecal and infusion techniques. Implants of the compounds are also useful. The composition can be in a solid or semisolid form, for example pills, tablets, creams, gelatin capsules, capsules, suppositories, soft gelatin capsules, gels, membranes, and tubelets. For local use, those preparations in the form of creams or ointments for topical use or in the form of sprays can be considered; for inhalant uses, preparations in the form of sprays, for example nose sprays, can be considered. The preferred route of administration is intramuscular injection: The patient being treated by in vivo administration is a warm-blooded animal and, in particular, mammals including man, sheep, horses, cattle, pigs, dogs, cats, rats and mice. Alternatively, the present invention can be used in vitro to treat cancer or cancer cells. The pharmaceutically acceptable carriers, diluents, adjuvants and vehicles as well as implant carriers generally refer to inert, non-toxic solid or liquid fillers, diluents or encapsulating material not reacting with the active ingredients of the invention.

The doses can be single doses or multiple doses over a period of several days. The treatment generally has a length proportional to the length of the disease process and drug effectiveness and the patient species being treated. The dosage requirements of the pharmaceutical compositions according to the present invention will vary with the particular pharmaceutical compositions employed, the route of administration and the particular cancer and cancer patient being treated. Treatment will generally be initiated with small dosages less than the optimum dose of the compound. Thereafter, the dosage is increased until the optimum effect under the circumstances is reached. In general, the pharmaceutical compositions according to the present invention are most administered at a concentration that will generally afford effective results without causing excessive harmful or deleterious side effects. The amount of the pharmaceutical composition that will be effective in treatment can be determined by standard clinical techniques, known to a worker skilled in the art [for example, see Remington's Pharmaceutical Sciences, 18th Edition, Mack Publishing Co., Easton, Pa. (1990)].

When administering the compound of the present invention parenterally, it will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various of the other ingredients, as desired.

A pharmacological formulation of the present invention can be administered to the patient in an injectable formulation containing any compatible carrier, such as various vehicle, adjuvants, additives, and diluents; or the compounds utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include: 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art.

The invention is further described in detail by reference to the following experimental examples. These examples are provided for the purpose of illustration only, and are not intended to be limiting unless otherwise specified. Thus, the invention should in no way be construed as being limited to the following examples, but rather, should be construed to encompass any and all variations which become evident as a result of the teaching provided herein.

Example 1

Study Objectives

The primary objective of the study was to compare overall survival time following initial treatment with a combination therapy of VIRULIZIN® plus gemcitabine versus placebo plus gemcitabine. Optional second-line therapy included continuation of VIRULIZIN® or placebo, alone or in combination with 5-FU or best supportive care.

Secondary objectives of the study included: (1) comparing the time to symptom progression between treatment groups; and (2) determining the overall safety of the trial regimens and to assess the safety of the combination therapies VIRULIZIN® plus gemcitabine and VIRULIZIN® plus 5-FU.

Additional secondary objectives of the study were: (1) to assess the pharmacokinetic profile of gemcitabine when used in combination with VIRULIZIN®; and (2) to assess plasma concentrations of 5-FU when given in combination with VIRULIZIN®.

Methodology

This was a double-blind, multicenter, randomized, 2-arm, parallel group, 3-stage trial. Median survival was the primary end-point calculated from Kaplan-Meier plots of survival of the Intention to Treat data set.

Stage 1

Eighteen patients were randomized either to VIRULIZIN® plus gemcitabine or to placebo plus gemcitabine. The blood pharmacokinetic profiles of gemcitabine and VIRULIZIN® were assessed by an independent (unblinded) pharmacokinetics assessor. Stage 1 was performed at selected sites. Immune stimulation assays were also to be performed in these patients.

Patients from Stage 1 were allowed to continue to Stage 2, and enrollment in Stage 2 was allowed to continue, because there were no observed drug interaction issues, as determined by the unblinded observer, based on the detection of no dose limiting toxicity, adverse events, pharmacokinetic evaluation, laboratory tests and vital signs.

Stage 2

Patients continued in Stage 2 until they developed intolerance to gemcitabine or demonstrated no clinical benefit (e.g., disease progression). An additional 417 patients enrolled in Stage 2 for a total of 435 patients enrolled in the study. One patient withdrew from study before being randomized and was censored, thus 434 patients were randomized onto the trial. The decision to discontinue patients from Stage 2 and move them into Stage 3 and to continue or discontinue study treatment was at the discretion of the investigator.

Stage 3

A total of 248 patients entered Stage 3. In Stage 3 patients originally randomized to VIRULIZIN® plus gemcitabine at Stage 1 (or Stage 2) received VIRULIZIN® plus 5-FU or best supportive care with or without VIRULIZIN® alone. Patients originally randomized to placebo plus gemcitabine received placebo with or without 5-FU or best supportive care with or without placebo. However, if the investigator believed further chemotherapy was not in the best interest of the patient (based on hematological profile, symptom progression or no evidence of clinical benefit), the patient continued to receive best supportive care, with or without continued injections of VIRULIZIN® or placebo. The first 18 patients entering Stage 3 and receiving VIRULIZIN® or placebo plus intravenous infusions of 5-FU were to have blood samples taken to assess the pre- and post-dose plasma concentrations of 5-FU.

At intervals throughout the study, samples were taken to assess the immunologic pharmacodynamic profile of VIRULIZIN®.

Number of Patients

Four hundred thirty five patients were enrolled in the study, 434 were randomized, and 431 patients were treated. The Intention to Treat analysis set consisted of 434 patients, the Efficacy Evaluable analysis set consisted of 377 patients, and the Safety analysis set consisted of 431 patients.

Diagnosis and Main Criteria for Inclusion

Male or female patients, aged 18 years or older, with advanced (unresectable or metastatic) pancreatic adenocarcinoma (tumor staging definition—tumor, lymph nodes, metastasis [TNM] stages II, III or IV) who had not received previous systemic chemotherapy, who had Eastern Cooperative Oncology Group (ECOG) Score 0, 1 or 2, and life expectancy greater than or equal to 12 weeks were included in the study.

Test Product, Dose, Mode of Administration

VIRULIZIN® or placebo was administered as intramuscular injections of 3 mL with dosing 3 times weekly (Monday, Wednesday, Friday) in Stages 1, 2 and 3.

Following pain stabilization screening, all randomized patients in Stages 1 and 2 received 30-minute intravenous infusions of gemcitabine at a dose of 1 g/m2 weekly for the first 7 weeks, followed by a week of rest. Subsequent cycles consisted of 28-day cycles with gemcitabine dosing on days 1, 8 and 15. Guidelines for dose reduction in case of toxicity were provided from the Official Product Prescribing Guidelines. Dosing continued until intolerance to gemcitabine developed, or there was symptom progression, or no evidence of clinical benefit. Patients then entered Stage 3, where they received 5-FU therapy 600 mg/m2 weekly using standard intravenous infusion regimen plus the same test product (VIRULIZIN® or placebo) as in Stages 1 and/or 2, or they received the same test product only (VIRULIZIN® or placebo) as in Stages 1 and/or 2 for as long as clinically indicated, or they received best supportive care only. The patient's physician made the decision concerning 5-FU chemotherapy or best supportive care.

Duration of Treatment

Treatment continued until 320 deaths had occurred across both treatment arms (blinded), or a 1-year follow-up of the last patient randomized had occurred, whichever was later. This was estimated to take 1.5 years accrual plus 1.0 year subsequent follow-up.

Criteria for Evaluation

Efficacy

Efficacy was evaluated based upon survival time, defined as the time from Baseline/Treatment Day 1 to the time of death from any cause. Time to progression of symptoms, consisting of: time to increase in pain (with consideration of analgesic consumption), time to deterioration in ECOG score, and time to weight loss.

Safety

Safety was evaluated based upon adverse events (AEs), laboratory tests, and vital signs.

Pharmacokinetics

Pharmacokinetic profiles of gemcitabine and some VIRULIZIN® constituents were evaluated in Stage 1. Plasma concentrations of 5-FU were determined in the first 18 patients to receive 5-FU plus VIRULIZIN® or placebo in Stage 3. The pharmacokinetics profiles of VIRULIZIN® constituents were not successfully determined.

Pharmacodynamics

Pharmacodynamics was evaluated based upon monocyte immune stimulation and natural killer cell function, but was not successfully determined.

SUMMARY OF RESULTS AND CONCLUSIONS

Overall survival was not statistically significantly different between patients treated with VIRULIZIN® plus gemcitabine compared to those treated with placebo plus gemcitabine. For those patients who continued to receive study treatment in Stage 3 of the study, there was a marked clinical and statistically significant survival benefit for patients in the VIRULIZIN® treatment arm.

Although the median overall survival results were not statistically significant, there was survival benefit in some analysis subsets for patients in the VIRULIZIN® treatment arm. Patients with study enrollment ECOG score of 0 or 1 treated with VIRULIZIN® and gemcitabine had greater median survival from time of randomization (7.4 months) than those with study enrollment ECOG score of 0 or 1 treated with placebo and gemcitabine (6.4 months). Patients in the Intention to Treat (ITT) analysis population with study enrollment ECOG score of 2 treated with VIRULIZIN® and gemcitabine had similar median survival from time of randomization (5.1 months, N=69) than those patients with study enrollment ECOG score of 2 treated with placebo and gemcitabine (5.1 months, N=67, p=0.6757). The Intention to Treat population had a considerable improvement in percentage of patient survival at 12 months for patients in the VIRULIZIN® treatment arm (30.4%) versus the placebo treatment arm (21.1%). Improvement in 12 months survival is more pronounced in the Efficacy Evaluable population.

Between treatment comparison of secondary efficacy variables failed to demonstrate significant differences, however, time to progression of pain from time of randomization in the Intention to Treat population tended to be increased in the ECOG score of 0 or 1 patients treated with VIRULIZIN® plus gemcitabine compared to patients receiving placebo plus gemcitabine (13.1 mo vs. 9.0 mo, p=0.0834). Key efficacy results are summarized in TABLES 2A, 2B, 2C, and 3 below. TABLE 2A. Analysis of Intention to Treat patient data set for survival from study enrollment to death from any cause of chemonaive patients with metastatic or locally advanced pancreatic cancer treated with VIRULIZIN® plus gemcitabine or placebo plus gemcitabine. Median survival in months [95% confidence interval (CI)]. Number of patients per group, n=.

TABLE 2A

| Survival in study Stages 1, 2, & 3) Intention to Treat patient data set | | | |
|---|---|---|---|
| Treatment | VIRULIZIN ® plus gemcitabine | Placebo plus gemcitabine | p value |
| Subset Variable | Median survival time from study enrollment to death from any cause [months (95% CI)], n = number of patients | | |
| Overall | 6.3 (5.6 to 7.4) n = 218 | 6.0 (5.1 to 7.0) n = 216 | 0.4018 |
| ECOG 0 or 1 | 7.4 (6.0 to 9.4) n = 149 | 6.4 (5.0 to 7.3) n = 149 | 0.2007 |
| ECOG 2 | 5.1 (3.2 to 6.2) n = 69 | 5.1 (4.1 to 6.8) n = 67 | 0.6757 |
| Locally advanced | 7.8 (6.8 to 11.5) n = 55 | 8.4 (7.1 to 11.2) n = 52 | 0.8949 |

TABLE 2A-continued

Survival in study Stages 1, 2, & 3) Intention to Treat patient data set

| Treatment | VIRULIZIN ® plus gemcitabine | Placebo plus gemcitabine | p value |
|---|---|---|---|
| Metastatic | 5.7 (5.1 to 6.8) n = 163 | 5.0 (4.3 to 6.0) n = 164 | 0.3661 |
| Patients participating in study Stage 3 | 11.2 (8.3 to 12.9) n = 125 | 7.5 (6.8 to 9.4) n = 123 | 0.0106 |
| | Percent 12-Month Survival [% (95% CI)] | | |
| Overall | 25.9 (19.9 to 31.9) | 17.7 (12.3 to 23.0) | |
| ECOG 0 or 1 | 30.4 (22.7 to 38.1) | 21.1 (14.3 to 28.0) | |
| Metastatic | 22.2 (15.7 to 28.7) | 13.3 (8.0 to 18.6) | |

Analysis of the primary and secondary study end-points of the Intention to Treat patient data set comparing the VIRULIZIN® plus gemcitabine treatment arm versus placebo plus gemcitabine treatment arm indicated statistical significance (two-sided test, P value less than 0.05) for survival from study enrollment until death from any cause. Similarly statistical comparisons of the patient sub-populations with low ECOG score of 0 or 1 at study enrollment, high ECOG score of 2 at study enrollment, locally advanced disease at study enrollment, and metastatic disease at study enrollment similarly failed to demonstrate statistically significant benefit measured by survival starting at study enrollment between the patients receiving VIRULIZIN® plus gemcitabine versus placebo plus gemcitabine. The only study subpopulation with a statistically significant greater survival of patients treated with VIRULIZIN® plus gemcitabine versus patients treated with placebo plus gemcitabine was that of patients participating in Stage 3 (P=0.0106) after completing Stage 1 and/or 2 of the study. This result shows that treatment with VIRULIZIN® for longer time period can increase the likelihood of survival versus placebo. The most likely way to prospectively select patients who will survival longer is to select patients with a Low ECOG score of 0 or 1.

The percent (%) of the Intention to Treat overall patient population, patients with Low ECOG score of 0 or 1 at study enrollment and patients with metastatic pancreatic cancer at study enrollment surviving at 12 months was greater for the patients treated with VIRULIZIN® plus gemcitabine than for the patients treated with placebo plus gemcitabine.

TABLE 2B. Analysis of Efficacy Evaluable patient data set for survival from time of study enrollment to death from any cause of chemonaive patients with metastatic or locally advanced pancreatic cancer treated with VIRULIZIN® plus gemcitabine or placebo plus gemcitabine.

TABLE 2B

Survival in study Stages 1, 2, & 3) Efficacy evaluable patient data set

| Treatment | VIRULIZIN ® plus gemcitabine n = 194 | Placebo plus gemcitabine n = 183 | p value |
|---|---|---|---|
| Subset Variable | Median survival time, study enrollment to death from any cause [months (95% CI)] n = number of patients | | |
| Overall | 6.8 (5.7 to 7.8) | 6.0 (5.1 to 7.0) | 0.1815 |
| ECOG 0 or 1 | 8.2 (6.5 to 10.4) | 6.3 (5.0 to 7.2) | 0.0630 |
| ECOG 2 | 5.1 (3.8 to 6.8) | 5.5 (4.3 to 7.4) | 0.7763 |
| Locally advanced disease | 7.8 (6.8 to 11.5) | 8.1 (7.1 to 11.2) | 0.9882 |
| Metastatic disease | 6.1 (5.3 to 7.4) | 5.0 (4.3 to 6.0) | 0.0831 |
| Patients participating in study Stage 3 | 11.2 (8.3 to 13.0) | 7.4 (6.8 to 8.6) | 0.0112 |

TABLE 2B-continued

Survival in study Stages 1, 2, & 3) Efficacy evaluable patient data set

| Treatment | VIRULIZIN ® plus gemcitabine n = 194 | Placebo plus gemcitabine n = 183 | p value |
|---|---|---|---|
| | Percent 12-Month Survival [% (95% CI)] | | |
| Overall | 27.2 (20.8 to 33.7) | 16.9 (11.2 to 22.6) | |
| ECOG 0 or 1 | 32.2 (23.9 to 40.6) | 20.1 (12.8 to 27.4) | |
| Metastatic | 24.2 (17.1 to 31.3) | 10.9 (5.4 to 16.4) | |

Analysis of the Efficacy Evaluable survival patient data set summarized in TABLE 2B supports similar conclusions to the analysis of the Intention to Treat data set. None of the primary and secondary study end-points of the Efficacy Evaluable patient data set comparing patient survival (study enrollment through death from any cause) for the VIRULIZIN® plus gemcitabine treatment arm versus placebo plus gemcitabine treatment arm achieved statistical significance (two-sided test, p value less than 0.05). The only study sub-population with a statistically significant greater survival of patients treated with VIRULIZIN® plus gemcitabine versus placebo plus gemcitabine was that of patients participating in Stage 3 (P=0.0112) after completing Stage 1 and/or 2 of the study. This result shows that treatment with VIRULIZIN® for longer time period can increase the likelihood of survival versus placebo.

The percent (%) of the Efficacy Evaluable overall patient population, patients with Low ECOG score of 0 or 1 at study enrollment and patients with metastatic pancreatic cancer at study enrollment surviving at 12 months was greater for the patients treated with VIRULIZIN® plus gemcitabine than for the patients treated with placebo plus gemcitabine.

TABLE 2C. Analysis of Intention to Treat survival data set of patients who continued study participation in study Stage 3 after Stage 1 and/or 2. Survival data is period from study enrollment until death from any cause. Patients were treated with VIRULIZIN® plus gemcitabine or placebo plus gemcitabine in Stage 1 and/or 2. Subset analyses compare patients with Low ECOG score of 0 and 1 versus High ECOG score of 2.

TABLE 2C

Survival in study Stages 1, 2 & 3 of ECOG 0 and 1 versus ECOG 2 populations Intention to Treat patient data set

| Treatment | VIRULIZIN ® plus gemcitabine during study Stage 1/2 | Placebo plus gemcitabine during study Stage 1/2 | P value |
|---|---|---|---|
| Subset Variable | Median survival time from study enrollment to death from any cause [months], n = number of patients | | |
| ECOG 0 or 1 | 10.42 n = 84 | 7.13 n = 78 | 0.00667 (Chi squared of 12.2 with 3 degrees of freedom) |
| ECOG 2 | 6.80 n = 41 | 6.31 n = 45 | |
| | ECOG 0 or 1 | ECOG 2 | |
| All patients participating in study Stage 3 (regardless of treatment) | 8.32 n = 162 | 6.31 n = 86 | 0.00946 (Chi squared of 6.7 with 1 degree of freedom) |

Analysis was performed on the 248 patients participating in Stage 3, comparing those with ECOG score of 0 or 1 versus ECOG score of 2 and treated with VIRULIZIN® plus gemcitabine versus placebo plus gemcitabine during study Stage 1 and/or 2. The patients with ECOG score of 0 or 1 and treated with VIRULIZIN® plus had median survival of 10.42 months, which is approximately 3 to 4 months greater median survival than the any of the other three groups in this comparison and resulting in a highly significant p value of 0.00667. This data supports that there is an additive effect of Low ECOG score and treatment with VIRULIZIN® versus placebo upon survival in the population of patients who stayed on study through Stage 3.

Analysis of survival during (study enrollment to death from any cause) of the patient subpopulation participating in Stage 3 of the study of the patients with ECOG score of 0 or 1 versus patients with an ECOG score of 2 at study enrollment indicates that the patients with an ECOG score of 0 or 1 survived significantly longer versus the patients with an ECOG score of 2 (P=0.00946) without regard to treatment in Stage 1, 2, or 3.

TABLE 3. Analysis of survival from entry into study Stage 3 to death from any cause of patients with metastatic or locally advanced pancreatic cancer treated in study Stage 1 and/or 2 with VIRULIZIN® plus gemcitabine or placebo plus gemcitabine followed in Stage 3 by treatment with VIRULIZIN® plus 5-FU or placebo plus 5-FU. Analysis of Intention to Treat patient data set.

TABLE 3

Median survival during study Stage 3 for Intention to Treat patient data set

| Stage 1 or 2 treatment group assignment | VIRULIZIN® plus gemcitabine | Placebo plus gemcitabine | P value |
|---|---|---|---|
| Subset Variable | Median survival time from entry into study Stage 3 to death from any cause months, n = number of patients | | |
| Stage 3 treatment | VIRULIZIN® with or without 5-FU | Placebo with or without 5-FU | |
| Overall | 3.02 n = 125 | 2.96 n = 123 | 0.253 |
| ECOG 0 or 1 | 4.1 n = 84 | 3.19 n = 78 | 0.109 (Chi squared of 6.1 with 3 degrees of freedom) |
| ECOG 2 | 1.97 n = 41 | 2.9 n = 45 | |
| | ECOG score of 0 or 1 | ECOG score of 2 | |
| Overall (any Stage 3 treatment) | 3.32 n = 162 | 2.63 n = 86 | 0.0801 (Chi squared of 3.1 with 1 degree of freedom) |
| Stage 3 treatment | VIRULIZIN® plus 5-FU | Placebo plus 5-FU | |
| Overall | 4.08 n = 34 | 3.22 n = 27 | 0.0415 |
| ECOG 0 or 1 | 4.40 n = 25 | 2.94 n = 16 | 0.006122 (Chi squared of 7.5 with 1 degree of freedom) |
| ECOG 2 | 2.63 n = 9 | 3.42 n = 11 | |

Analysis of all patients treated in Stage 3 with VIRULIZIN® with or without 5-FU versus all patients treated with placebo with or without 5-FU during Stage 3 indicates no significant difference in median survival between the two treatment groups (P=0.253). When this patient data was partitioned by ECOG score of 0 or 1 versus ECOG score of 2 at study enrollment the median survival of the patients with ECOG score of 0 or 1 receiving VIRULIZIN® with or without 5-FU was greater than the other groups, but not statistically significantly increased (p=0.109). The median survival in Stage 3 of the patients in receiving VIRULIZIN® plus 5-FU (4.08 months) was statistically significantly greater versus those patients receiving placebo plus 5-FU during Stage 3 (3.22 months, p=0.0415). Those patients with ECOG score of 0 or 1 at study enrollment treated with VIRULIZIN® plus 5-FU (4.40 months) was highly statistically significantly greater versus those patients with ECOG score of 0 or 1 who received placebo plus 5-FU during study Stage 3 (2.94 months, p=0.006122).

Four (17%) of the 25 patients with ECOG score of 0 or 1 at enrollment who received VIRULIZIN® plus 5-FU in study Stage 3 were alive and survival status was censored at the end of the study data collection period (12 to 20 months after entry onto Stage 3). None (0%) of the 16 patients of ECOG 0 or 1 score at enrollment In general, the addition of VIRULIZIN® to standard gemcitabine therapy for first-line treatment of patients with advanced or metastatic pancreatic adenocarcinoma did not appear to increase the risks or toxicities associated with gemcitabine or to introduce any clinically significant new risks or toxicities; similarly, patients who proceeded to second-line therapy with 5-FU and VIRULIZIN®.

The most common Adverse Events occurred with similar frequencies and intensities between treatment arms and are summarized in Table 4 below.

TABLE 4. Adverse Events observed in this Phase III randomized, placebo controlled clinical trial of patients with advanced pancreatic cancer treated in Stages 1 and 2 of the clinical trial with VIRULIZIN® plus gemcitabine or placebo plus gemcitabine. Patients continuing on to Stage 3 of this trial were treated in stage 3 with test product (VIRULIZIN® or placebo plus 5-FU, test product only (VIRULIZIN® or placebo) with best supportive care, or best supportive care only. Test product assignment (VIRULIZIN® or placebo) in Stage 3 continued in as randomized in Stages 1 or 2.

TABLE 4

| | VIRULIZIN® plus Gemcitabine Total of 217 patients | | Placebo plus Gemcitabine Total of 214 patients | |
|---|---|---|---|---|
| Preferred Term | Number (%) of Patients | Number of Events | Number (%) of Patients | Number of Events |
| Gastro-intestinal | | | | |
| Abdominal pain (not otherwise specified) | 65 (30.0) | 143 | 56 (26.2) | 96 |
| Abdominal pain upper | 19 (8.8) | 28 | 25 (11.7) | 35 |
| Constipation | 40 (18.4) | 56 | 40 (18.7) | 57 |
| Diarrhea (not otherwise specified) | 41 (18.9) | 126 | 46 (21.5) | 79 |
| Nausea | 85 (39.2) | 237 | 90 (42.1) | 269 |
| Vomiting (not otherwise specified) | 53 (24.4) | 127 | 63 (29.4) | 141 |
| Constitutional | | | | |
| Anorexia | 52 (24.0) | 73 | 51 (23.8) | 71 |
| Ascites | 25 (11.5) | 31 | 38 (17.8) | 51 |
| Dehydration | 23 (10.6) | 27 | 19 (8.9) | 26 |
| Disease progression (not otherwise specified) | 17 (7.8) | 17 | 25 (11.7) | 25 |
| Fatigue | 70 (32.3) | 127 | 77 (36.0) | 178 |
| Headache (not otherwise specified) | 24 (11.1) | 61 | 14 (6.5) | 42 |

TABLE 4-continued

| Preferred Term | VIRULIZIN ® plus Gemcitabine Total of 217 patients | | Placebo plus Gemcitabine Total of 214 patients | |
|---|---|---|---|---|
| | Number (%) of Patients | Number of Events | Number (%) of Patients | Number of Events |
| Edema peripheral | 55 (25.3) | 81 | 52 (24.3) | 76 |
| Pyrexia | 79 (36.4) | 194 | 65 (30.4) | 184 |
| Rigors | 21 (9.7) | 32 | 33 (15.4) | 97 |
| Weakness | 56 (25.8) | 109 | 51 (23.8) | 82 |
| Weight decreased | 35 (16.1) | 50 | 26 (12.1) | 38 |
| Back pain | 29 (13.4) | 46 | 21 (9.8) | 30 |
| Hematological and Laboratory Abnormalities | | | | |
| Alanine aminotransferase increased | 27 (12.4) | 36 | 15 (7.0) | 21 |
| Anemia (not otherwise specified) | 103 (47.5) | 250 | 94 (43.9) | 206 |
| Aspartate aminotransferase increased | 24 (11.1) | 32 | 19 (8.9) | 27 |
| Blood alkaline phosphatase increased (not otherwise specified) | 27 (12.4) | 42 | 21 (9.8) | 28 |
| Leukopenia (not otherwise specified) | 23 (10.6) | 54 | 29 (13.6) | 67 |
| Neutropenia | 69 (31.8) | 238 | 69 (32.2) | 212 |
| Thrombocytopenia | 66 (30.4) | 188 | 64 (29.9) | 196 |
| Other Common Events | | | | |
| Rash (not otherwise specified) | 23 (10.6) | 27 | 20 (9.3) | 26 |
| Dyspnea (not otherwise specified) | 32 (14.7) | 44 | 33 (15.4) | 46 |
| Jaundice (not otherwise specified) | 25 (11.5) | 29 | 25 (11.7) | 30 |

TABLE 4 summarizes the treatment-related AEs. They were generally low considering the patient population and similar between treatment arms. In general, the frequencies of SAEs, discontinuations due to AEs, and AEs with an outcome of death were similar between treatment groups. An increase in the number of cardiac SAEs was observed among patients receiving VIRULIZIN® plus gemcitabine (8.8% vs. 2.8%), but these increased events were not considered treatment related.

Hematology and clinical chemistry results were highly variable, but there was no clinically significant difference between treatment groups. Vital signs, physical examination results, and concomitant medication usage were not unexpected for this patient population and were generally similar between treatment groups. These results together with previous clinical trial experiences indicate that VIRULIZIN® contributed little if any toxicity to the treatment of these patients when used in combination with chemotherapy (gemcitabine or 5-FU) or when administered as a single agent.

The attempt to estimate natural killer (NK) cell levels by assessing lytic units was significantly incomplete and demonstrated no clear trends in either treatment group.

FIGS. 1 through 14 summarize the statistical analysis of the clinical study results for the Phase 3 double-blind, randomized trial in patients with advanced pancreatic cancer using VIRULIZIN® plus gemcitabine versus placebo plus gemcitabine that allowed optional continued study participation using the test product to which the patient was previously randomized (VIRULIZIN® or placebo) plus 5-FU, test product (VIRULIZIN® or placebo) only, or best supportive care only following completion of treatment with gemcitabine.

In FIG. 1, the 218 patients receiving VIRULIZIN® plus gemcitabine in study Stages 1 and/or 2 had a median overall survival of 6.3 months versus the 216 patients receiving placebo plus gemcitabine in study stages 1 and/or 2 with a median overall survival of 6.0 months which is not statistically significant, p=0.4018 This Phase 3 trial failed to meet this primary study endpoint of a significant increase in overall survival for the VIRULIZIN® plus gemcitabine versus placebo versus gemcitabine treatment group.

Figure 2:
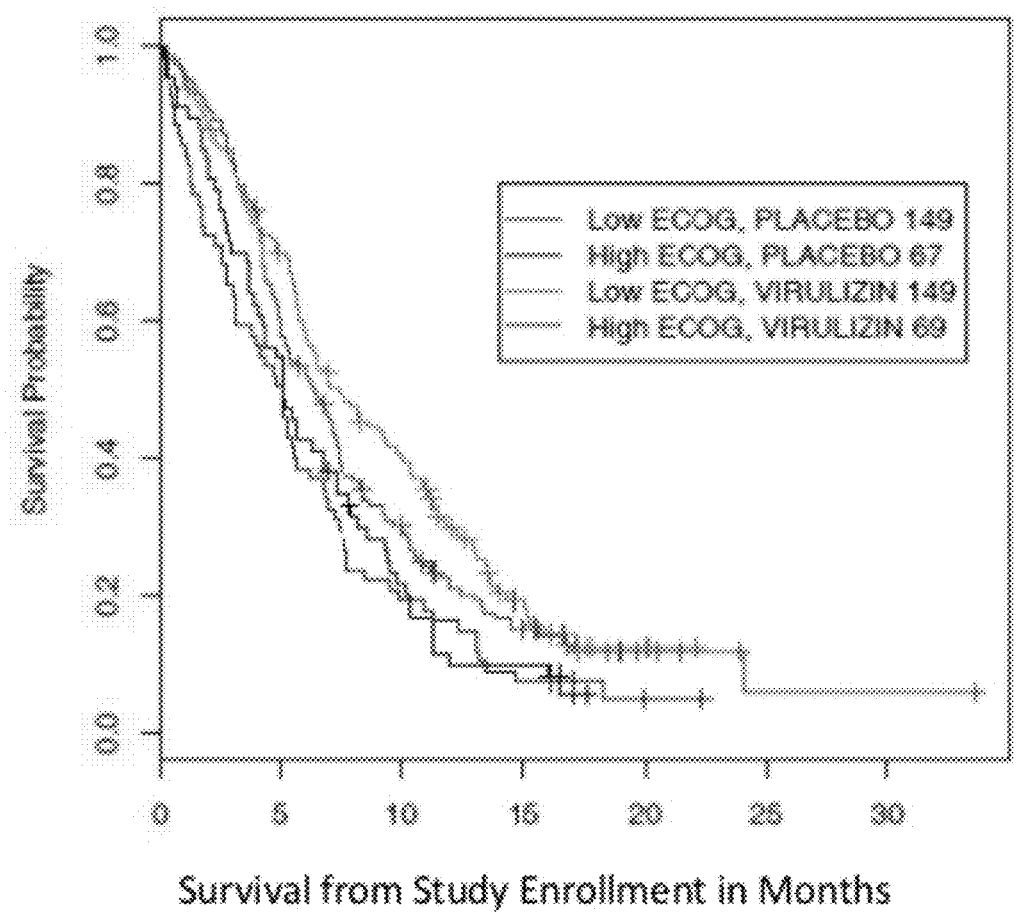
FIG. 2 is a graph comparing the Kaplan-Meier analysis of Overall Survival (OS) from the time of study enrollment until death from any cause or censor to follow-up for the 434 patients in the Intention to Treat population comparing the treatments of VIRULIZIN® plus gemcitabine versus placebo plus gemcitabine.

In FIG. 2, Patient survival was analyzed on the basis of ECOG score at study enrollment as Low ECOG score of 0 or 1) versus High ECOG score of 2). The OS of the 149 Low ECOG score patients treated with VIRULIZIN® plus gemcitabine during Stages 1 and 2 has a median OS of 7.4 months. The OS of the 149 Low ECOG score patients treated with placebo plus gemcitabine with median OS of 6.4 months didn't differ statistically significantly different with p=0.2007). The OS of the 69 patients with High ECOG score who were treated with VIRULIZIN® plus gemcitabine is also presented (median OS of 5.1 months). The OS of the 66 patients with High ECOG score who were treated with placebo plus gemcitabine (median OS of 6.4 months) didn't differ statistically with a p-value of 0.6757). There is no statistically significant difference in participation in median OS between patients receiving VIRULIZIN® plus gemcitabine versus patients receiving placebo plus gemcitabine when comparing the groups of patients with ECOG score of 0 or 1 or the patients with ECOG score of 2 at study enrollment.

Figure 3:
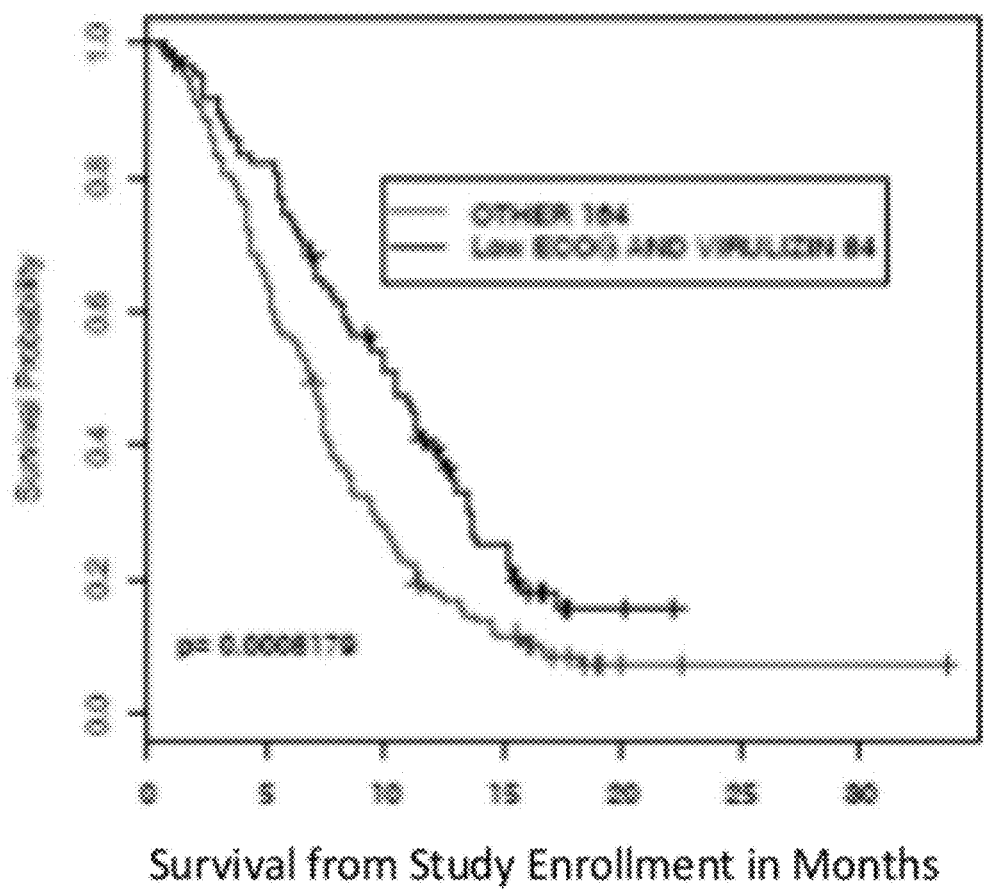
FIG. 3 is a graph comparing the Kaplan-Meier analysis of Overall Survival (OS) from the time of study enrollment until death from any cause or censor to follow-up for the 248 patients in the Intention to Treat population who participated in study Stage 3.

In FIG. 3, this analysis compares the treatments of VIRULIZIN® plus gemcitabine during study Stages 1 and/or 2 for the 84 patients with Low ECOG score of 0 or 1 at study enrollment (median OS=10.42 months) versus all 164 other patients participating in study Stage 3 (includes patients treated with VIRULIZIN® plus gemcitabine during study Stages 1 and/or 2 for patients with high ECOG score of 2 at study enrollment and all patients treated with placebo plus gemcitabine with Low or High ECOG score at study enrollment (median OS of 6.87 months, p=0.0008179). This very highly statistically significant difference in median OS for this subset of patients combined with the other analyses indicates that the population of patients with Low ECOG score of 0 or 1 treated VIRULIZIN® plus gemcitabine experience much of the increased survival observed in the population of patients participating in Stage 3 of this study.

Figure 4:
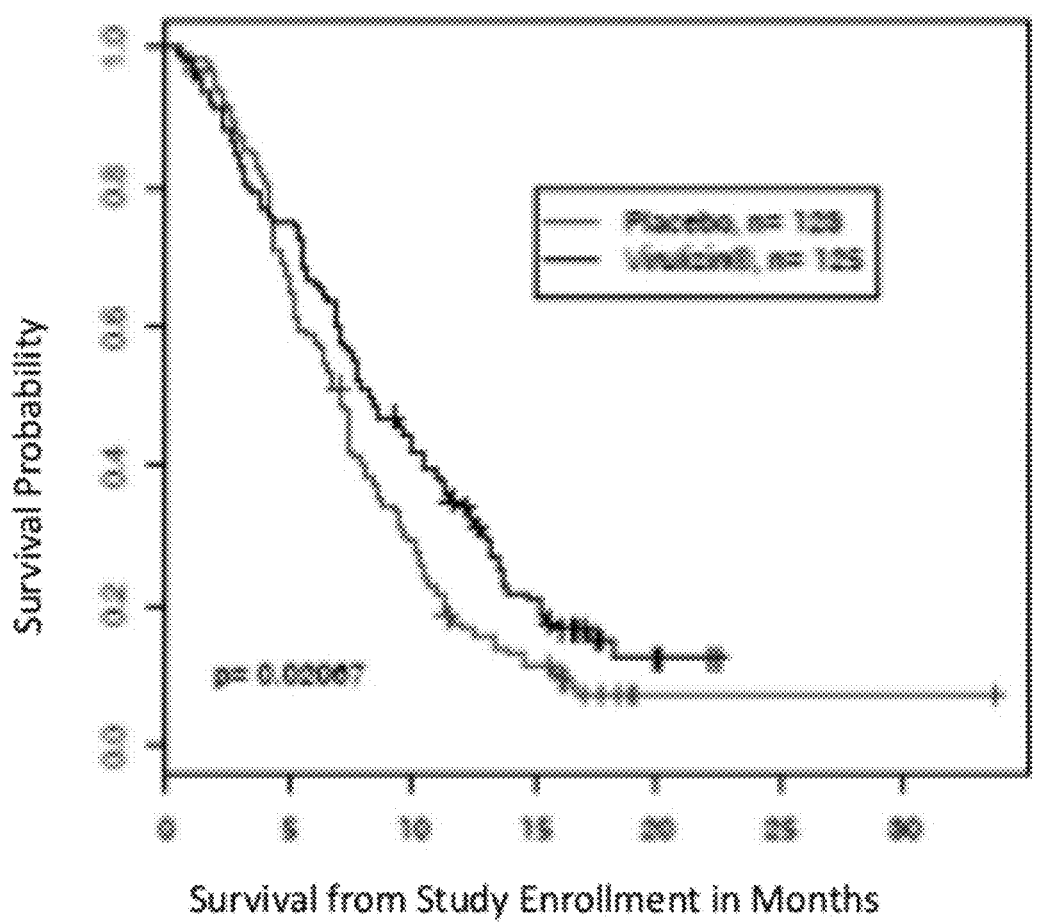
FIG. 4 is a graph comparing the Kaplan-Meier analysis of Overall Survival (OS) from the time of study enrollment until death from any cause or censor to follow-up for the 248 patients in the Intention to Treat population who participated in study Stage 3.

In FIG. 4, the median OS (11.2 months) for the 125 patients treated with VIRULIZIN® plus gemcitabine during study Stages 1 and/or 2 is statistically significantly greater than the median OS (7.5 months) of the 123 patients treated with placebo plus gemcitabine during study Stages 1 and/or 2. The p value of 0.0106 indicates that for the 248 patients who participated in study Stage 3 the patients treated with VIRULIZIN® had greater median OS. This result indicates that patients who received VIRULIZIN® versus placebo for a longer time period experienced more clinical benefit or that significant clinical benefit of treatment with VIRULIZIN® versus placebo occurred during study Stage 3. During Stage 3 VIRULIZIN® or placebo (blinded) could be continued as salvage treatment with or without 5-FU or patients received only best supportive care.

Figure 5:
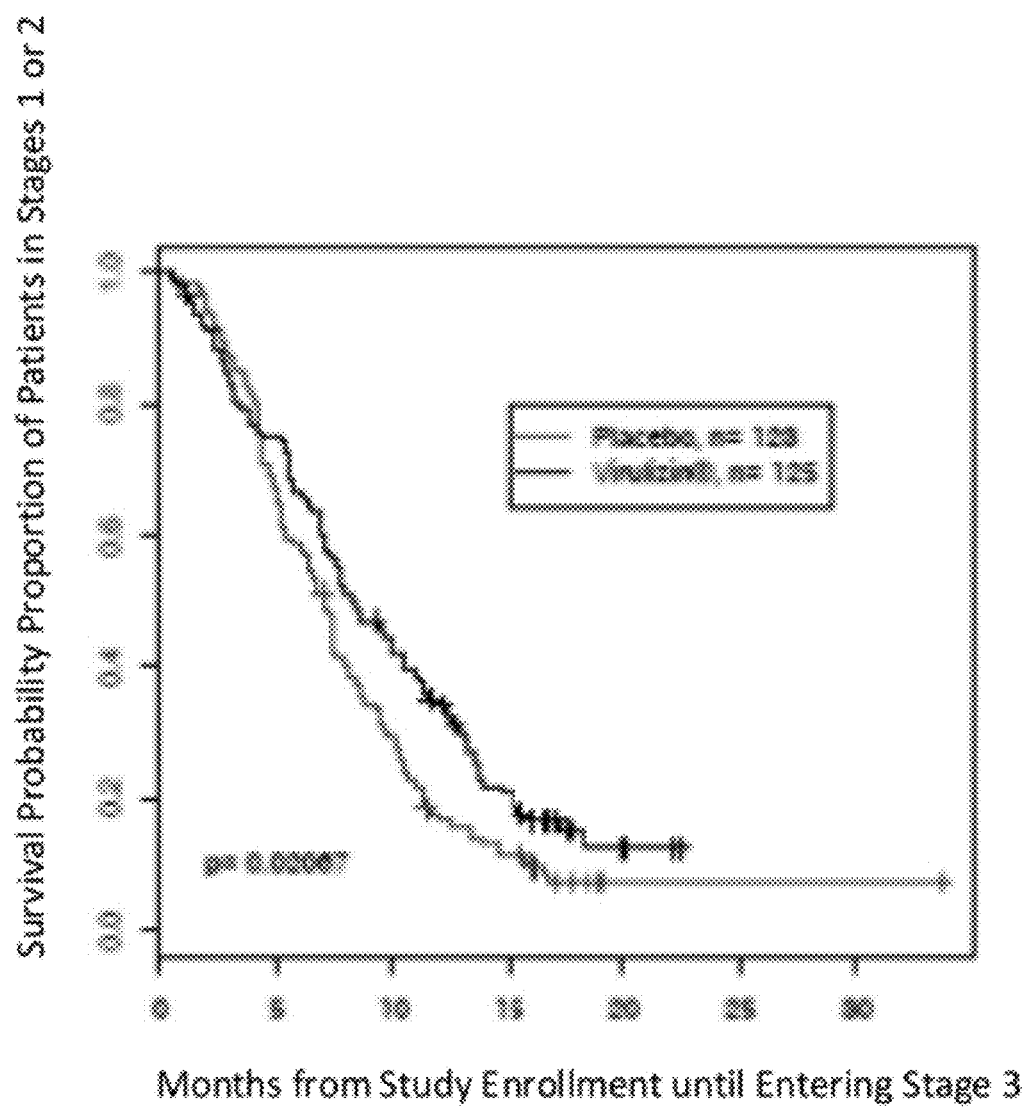
FIG. 5 is a graph comparing the Kaplan-Meier estimation of duration of participation in study Stages 1 and/or 2 from the time of study enrollment until patients ended gemcitabine treatment and entered study Stage 3 for the 248 patients (Intention to Treat population) who participated in study Stage 3.

In FIG. 5, the 125 patients treated with VIRULIZIN® plus gemcitabine during study Stages 1 and/or 2 have a median duration of participation in study Stages 1 and/or 2 of 8.32 months. The 123 patients treated with placebo plus gemcitabine during study Stages 1 and/or 2 have a median duration of participation in study Stages 1 and/or 2 of 6.31 months, p=0.00943. This analysis indicates that when the study Stage 3 patient population is segregated by test product treatment, the median duration of participation in study Stages 1 and/or 2 of the of patients treated with VIRULIZIN® plus gemcitabine is statistically significantly greater than the median duration of participation in study Stages 1 and/or 2 for the patients Placebo plus gemcitabine. This increase treatment interval could be attributed to reduced toxicity and/or increase efficacy of the VIRULIZIN® plus gemcitabine treatment increasing the time gemcitabine could be used during stages 1 and/or 2 of the study.

Figure 6:
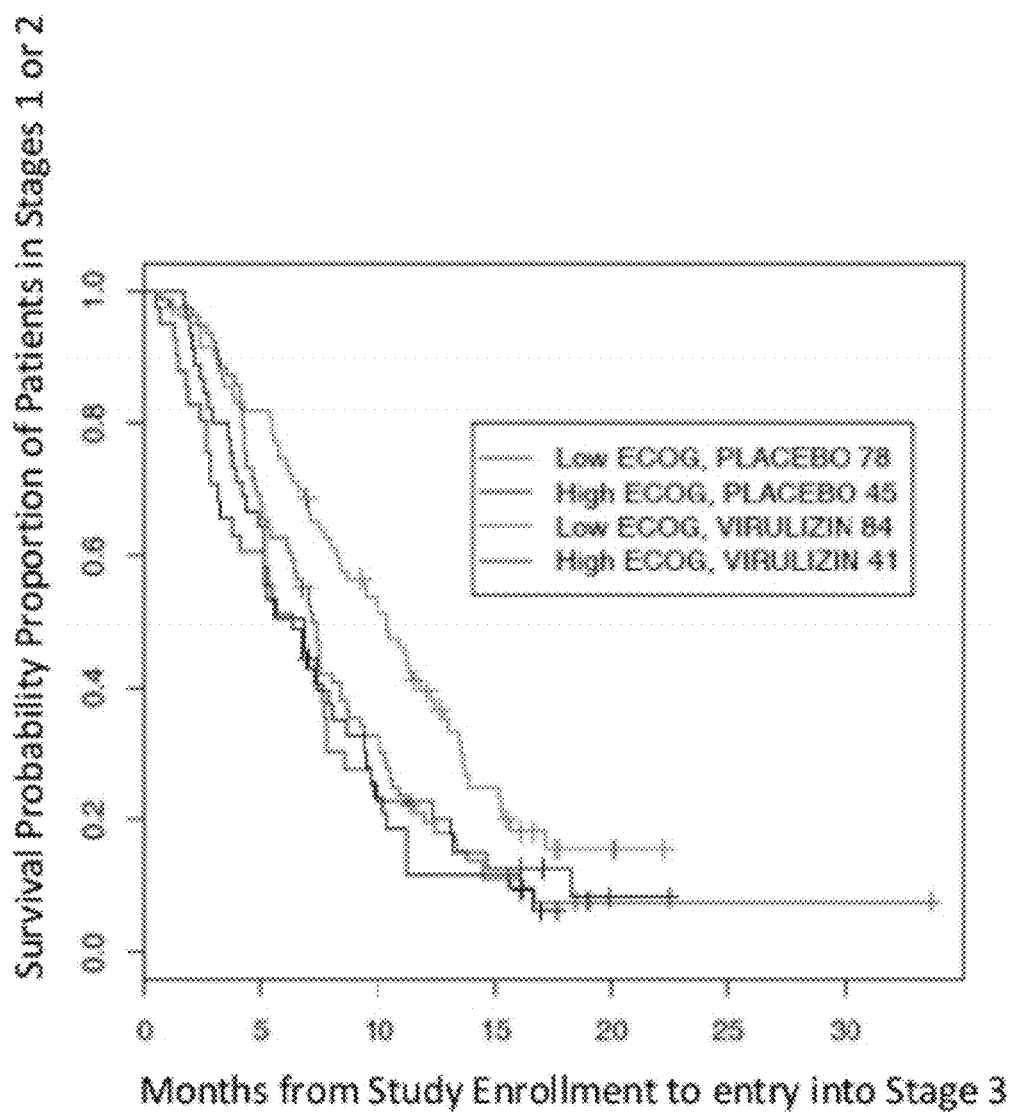
FIG. 6 is a graph comparing the Kaplan-Meier estimations of duration of participation in study Stages 1 and/or 2 (from the time of study enrollment until entry into study Stage 3) for the Intention to Treat population of 248 patients who participated in the study Stage 3.

In FIG. 6, the study treatments (VIRULIZIN® plus gemcitabine versus placebo plus gemcitabine) were compared and the patient treatment groups were segregated on the basis of ECOG score at study enrollment (Low ECOG score of 0 or 1 versus High ECOG score of 2). The plots are of the duration of participation in study Stages 1 and/or 2 for: The 84 patients with Low ECOG score who were treated with VIRULIZIN® plus gemcitabine (median duration of participation in study Stages 1 and/or 2 of 10.42 months), the 41 patients with High ECOG score who were treated with VIRULIZIN® plus gemcitabine (median duration of participation in study Stages 1 and/or 2 of 6.8 months), the 78 patients with Low ECOG score who were treated with placebo plus gemcitabine (median duration of participation in study Stages 1 and/or 2 of 7.13 months), and the 45 patients with High ECOG score who were treated with placebo plus gemcitabine (median duration of participation in study Stages 1 and/or 2 of 6.31 months.) The calculated chi squared is 12.2 on 3 degrees of freedom with p value of 0.00667. This result indicates that the median duration of participation in study Stages 1 and/or 2 for the patient population participating in study Stage 3 is significantly greater for patients with Low ECOG score of 0 or 1 at study enrollment who were treated with VIRULIZIN® plus gemcitabine. The patients with Low ECOG score at study enrollment who were treated VIRULIZIN® plus gemcitabine have a median survival 3.29 months greater than the patients with a Low ECOG score at study enrollment who were treated placebo plus gemcitabine. Patients participating in Stage 3 of the trial continued on the same test product assignment (either VIRULIZIN® or placebo) as in study Stage 1 and/or 2. In study Stage 3 patients were treated with test product with or without 5-FU or best supportive care only.

Figure 7:
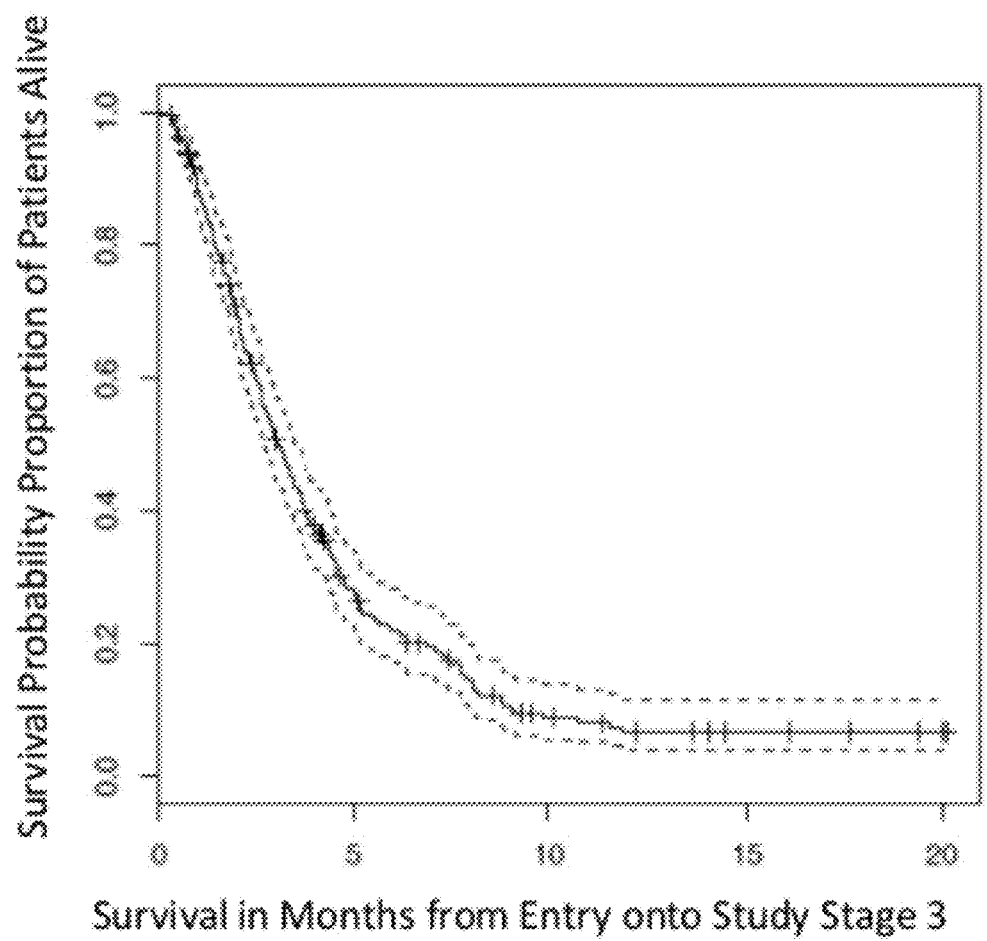
FIG. 7 is a graph presenting the Kaplan-Meier survival plots during study Stage 3 for the Intention to Treat population of 248 patients participating in study Stage 3 from the time of entry onto study stage 3 until death from any cause or censor from survival follow-up.

In FIG. 7, the median survival estimate during study Stage 3 for all patients participating in study Stage 3 is 3.02 months.

Figure 8:
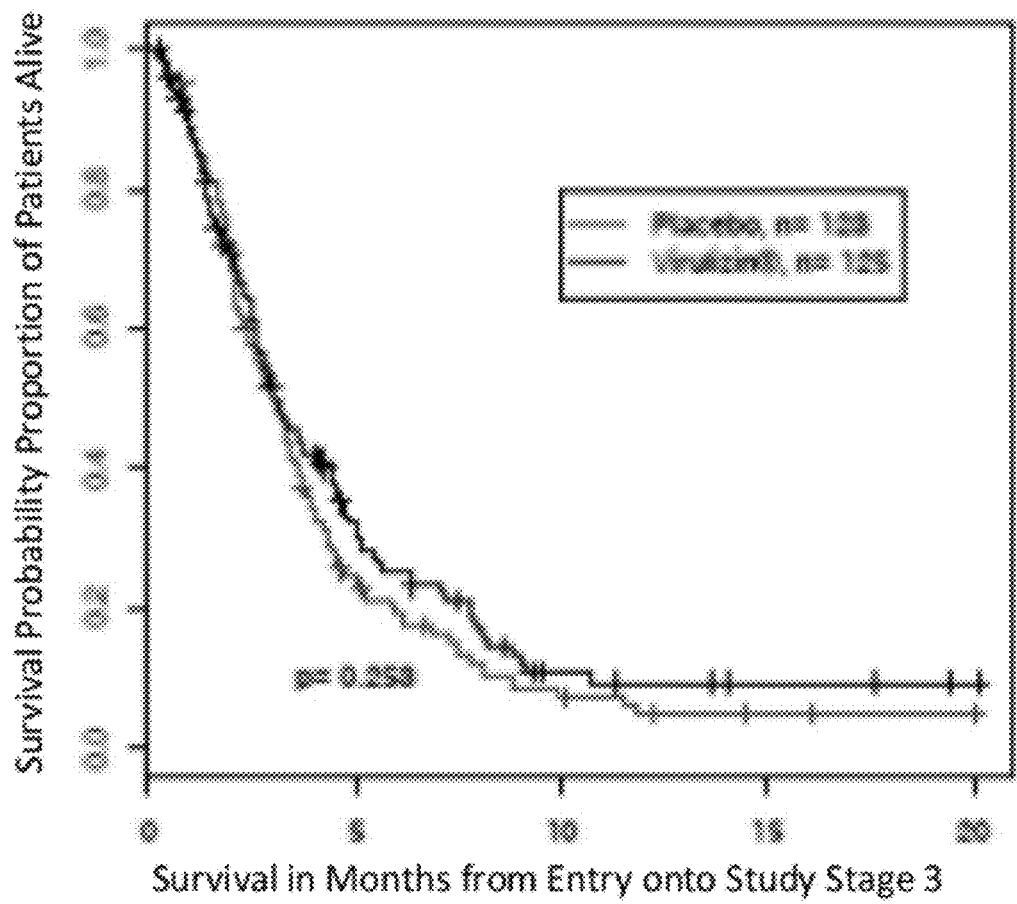
FIG. 8 is a graph comparing the Kaplan-Meier estimations of survival during study Stage 3 for the Intention to Treat population of 248 patients who participated in study Stage 3 from the time of entry onto study Stage 3 until death from any cause or censor from follow-up.

In FIG. 8, one plot is of the survival in study Stage 3 of the 125 patients who were treated with VIRULIZIN® plus gemcitabine during study Stages 1 and/or 2 and another plot is of the survival in study Stage 3 of the 123 patients who were treated with placebo plus gemcitabine during study Stages 1 and/or 2. Median survival during study Stage 3 (from enrollment in study Stage 3) is not significantly different between the patients treated with VIRULIZIN® plus gemcitabine in study Stages 1 and/or 2 (median study Stage 3 survival was 3.02 months) versus the median survival of patients treated with placebo plus gemcitabine in study Stages 1 and/or 2 (median Stage 3 survival was 2.96 months, p=0.253). Patients participating in Stage 3 of the trial continued on the same test product assignment of either VIRULIZIN® or placebo as in study Stage 1 and/or 2. In study Stage 3 patients were treated with test product with or without 5-FU or only best supportive care.

Figure 9:
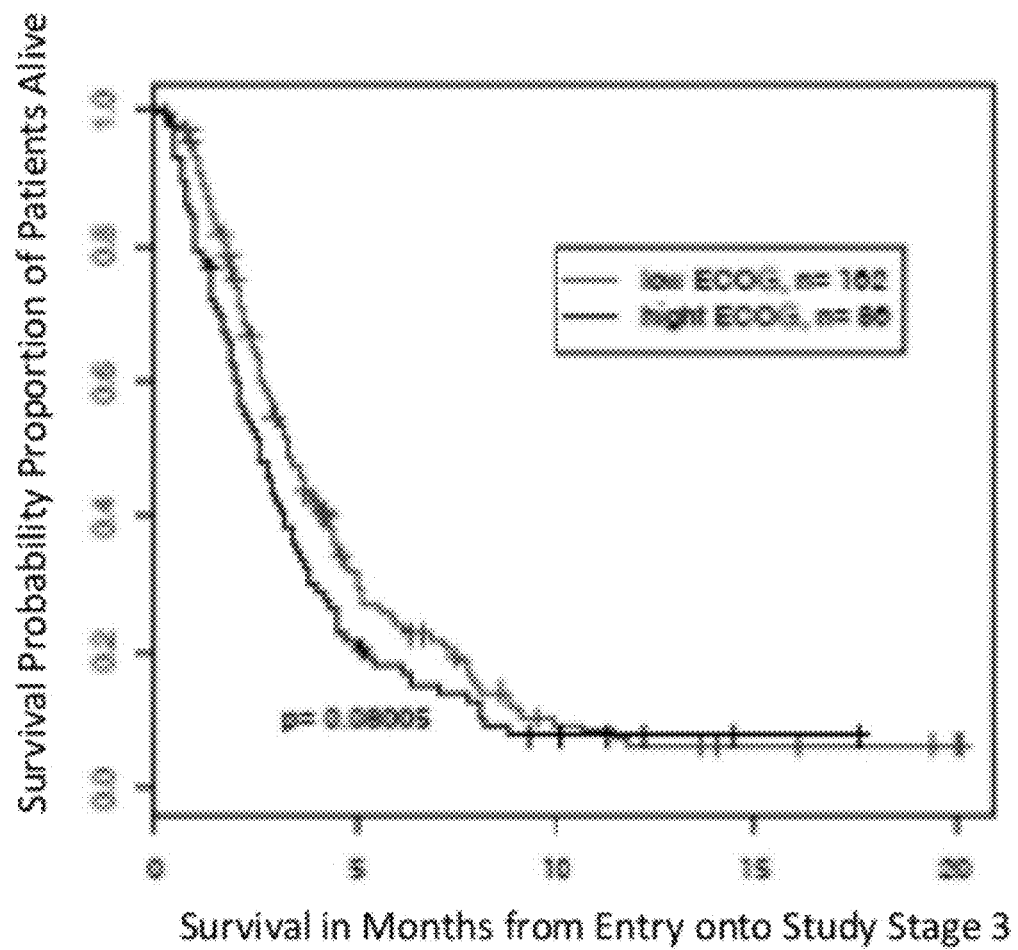
FIG. 9 is a graph comparing the Kaplan-Meier estimations of Stage 3 from the time of entry onto study Stage 3 until death from any cause or censor from follow-up for the patients with Low ECOG score of 0 or 1 at study enrollment versus the patients with High ECOG score of 2 at study enrollment.

In FIG. 9, a total of 248 patients of the Intention to Treat population participated in study Stage 3 and received VIRULIZIN® plus gemcitabine or placebo plus gemcitabine in study Stages 1 and/or 2. One plot summarizes survival of patients in study Stage 3 for the 162 patients with Low ECOG score of 0 or 1 at study enrollment (median survival in Stage 3 of 3.32 months). Another plot summarizes the survival in study Stage 3 for the 66 patients with High ECOG score of 2 at study enrollment (median Stage 3 survival of 2.63 months). The p value of 0.08005 for the comparison of the median survival in study Stage 3 of the patients with Low ECOG versus High ECOG score indicates that the patients with Low ECOG score at study entry with patients with High ECOG score at study entry irrespective of study treatment, the median survival during study Stage 3 of the median survival of patients with Low ECOG score was not statistically significantly greater than for Stage 3 survival for the patients with High ECOG score.

Figure 10:
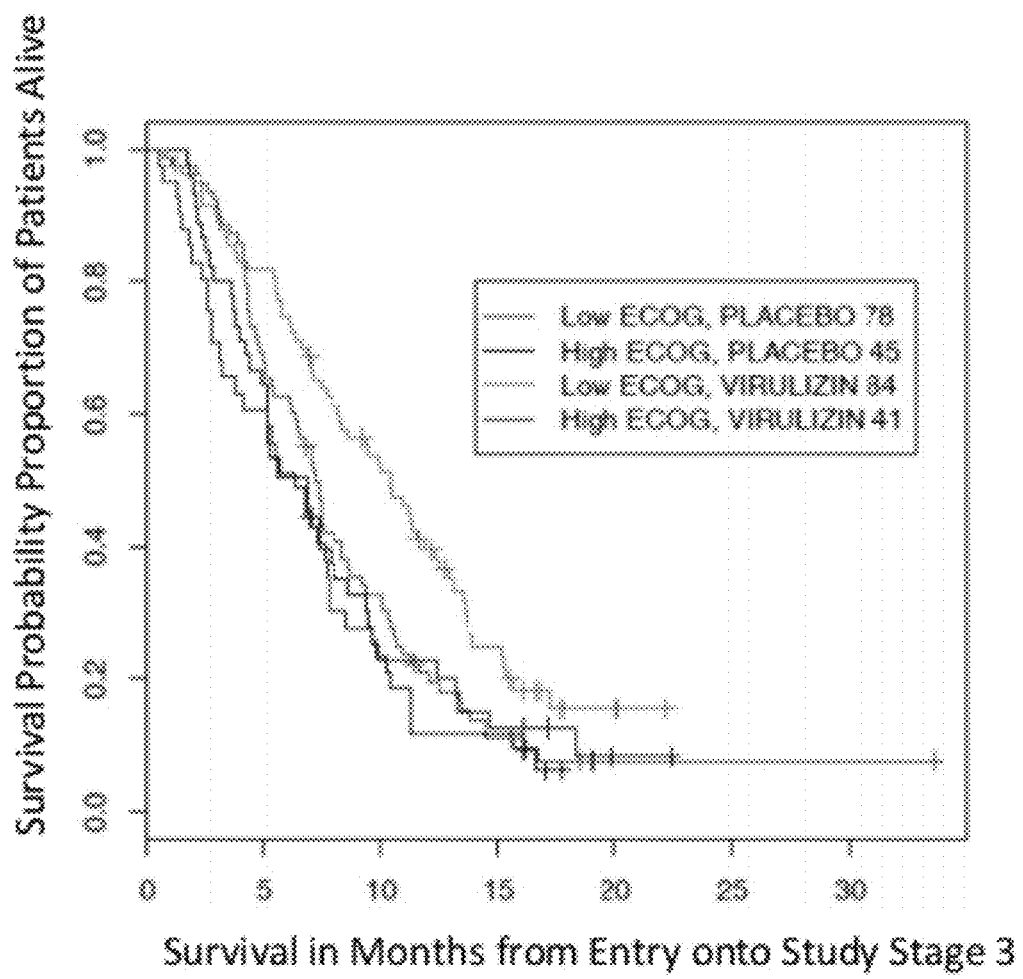
FIG. 10 is a graph comparing the Kaplan-Meier estimations of survival during study Stage 3 for the 248 patients of the Intention to Treat population analyzed by their study Stage 1 and/and or 2 treatment (VIRULIZIN® plus gemcitabine versus placebo plus gemcitabine) and by ECOG score at study enrollment (Low ECOG score of 0 or 1 versus High ECOG score of 2) from the time of entering study Stage 3 until death from any cause or censor from follow-up for survival.

In FIG. 10, one plot illustrates the survival in study Stage 3 of the 84 patients who were treated with VIRULIZIN® plus gemcitabine in study Stages 1 and/or 2 and had Low ECOG score at study enrollment (median survival in study Stage 3 of 3.19 months.) Another plot illustrates the survival in study Stage 3 of the 41 patients who were treated with VIRULIZIN® plus gemcitabine in Stages 1 and/or 2 and had High ECOG score at study enrollment (median survival in study Stage 3 of 2.79 months.) Another plot illustrates the survival in study Stage 3 of the 78 patients who were treated with placebo plus gemcitabine in Stages 1 and/or 2 and had Low ECOG score at study enrollment (median survival in study Stage 3 of 3.19 months.) Another plot illustrates the survival in study Stage 3 of the 41 patients who were treated with placebo plus gemcitabine in Stages 1 and/or 2 and had High ECOG score at study enrollment (median survival in study Stage 3 of 2.79 months.) Patients participating in Stage 3 of the trial continued on the same test product assignment of either VIRULIZIN® or placebo as in study Stage 1 and/or 2. In study Stage 3 patients were treated with test product with or without 5-FU or only best supportive care.

Figure 11:
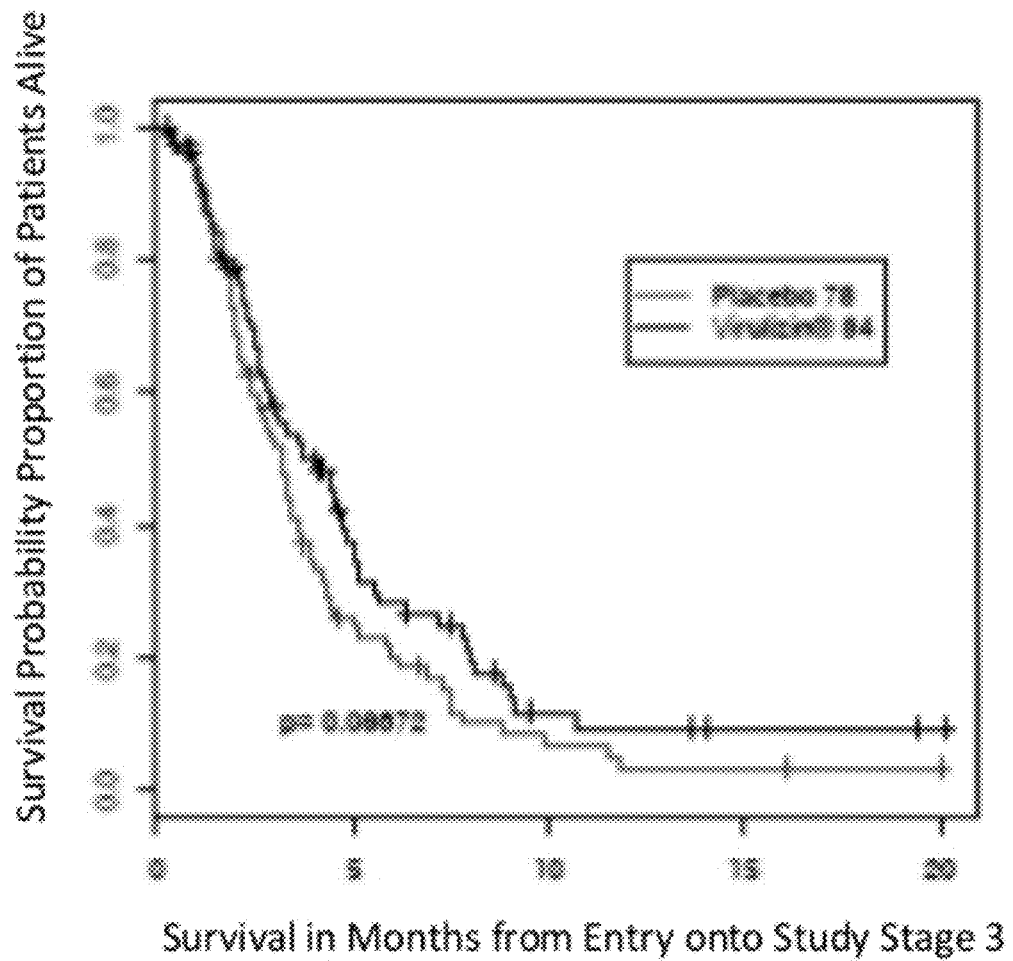
FIG. 11 is a graph comparing the Kaplan-Meier estimations of survival from the time of entry onto study Stage 3 until death from any cause or censor from follow-up for the 162 patients in the Intention to Treat population with Low ECOG score of 0 or 1 at study enrollment who participated in study Stage 3.

In FIG. 11, one plot is of the survival of the 84 patients of these patients with Low ECOG score at enrollment who were treated with VIRULIZIN® plus gemcitabine in study Stage 1 and/or 2 (median survival in the study Stage 3 of 3.75 months.) Another plot is of the survival of the 78 patients with Low ECOG score of 0 or 1 who were treated with placebo plus gemcitabine (median survival in the study Stage 3 of 3.19 months.) Statistical analysis resulted in a p value of 0.08672 indicating no significant difference in survival of these patient populations. Patients participating in Stage 3 of the trial continued on the same test product assignment of either VIRULIZIN® or placebo as in study Stage 1 and/or 2. In study Stage 3 patients were treated with test product with or without 5-FU or only best supportive care.

Figure 12:
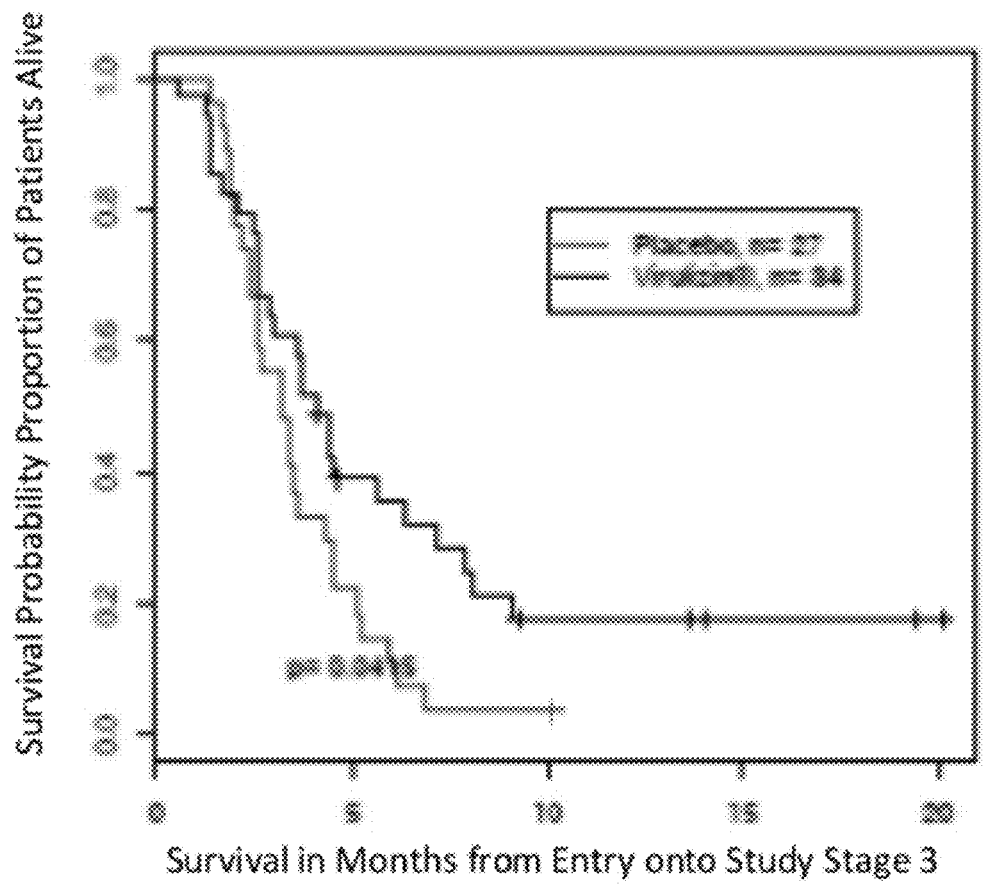
FIG. 12 is a graph comparing the Kaplan-Meier estimations of survival during study Stage 3 of the Intention to Treat population patients who were treated with 5-FU during Stage 3

In FIG. 12, the survival interval for this analysis was from the time of enrollment in study Stage 3 until death from any cause or censor from follow-up. Included are all of the 61 patients who were treated with VIRULIZIN® plus 5-FU (34 patients) or placebo plus 5-FU (27 patients) during study Stage 3. During study Stages 1 and/or 2 these patients were treated with either VIRULIZIN® plus gemcitabine (34 patients) or placebo plus gemcitabine (27 patients) after completing study stages 1 and/or 2. One plot is of the survival in Stage 3 of the 34 patients treated with VIRULIZIN® plus 5-FU during study stage 3 (median survival in Stage 3 of 4.08 months). Another plot is of the survival in Stage 3 of the 27 patients treated with placebo plus 5-FU during study Stage 3. Statistical analysis of the median survivals of these patients indicates that the median survival in study Stage 3 of the patients treated with VIRULIZIN® plus 5-FU is moderately statistically significantly greater than the median survival in Stage 3 of the patients treated with placebo plus 5-FU with a p-value of 0.0415. Patients participating in Stage 3 of the trial continued on the same test product assignment of either VIRULIZIN® or placebo as in study Stage 1 and/or 2. During study Stage 3 patients were treated with test product with or without 5-FU or only best supportive care.

Figure 13:
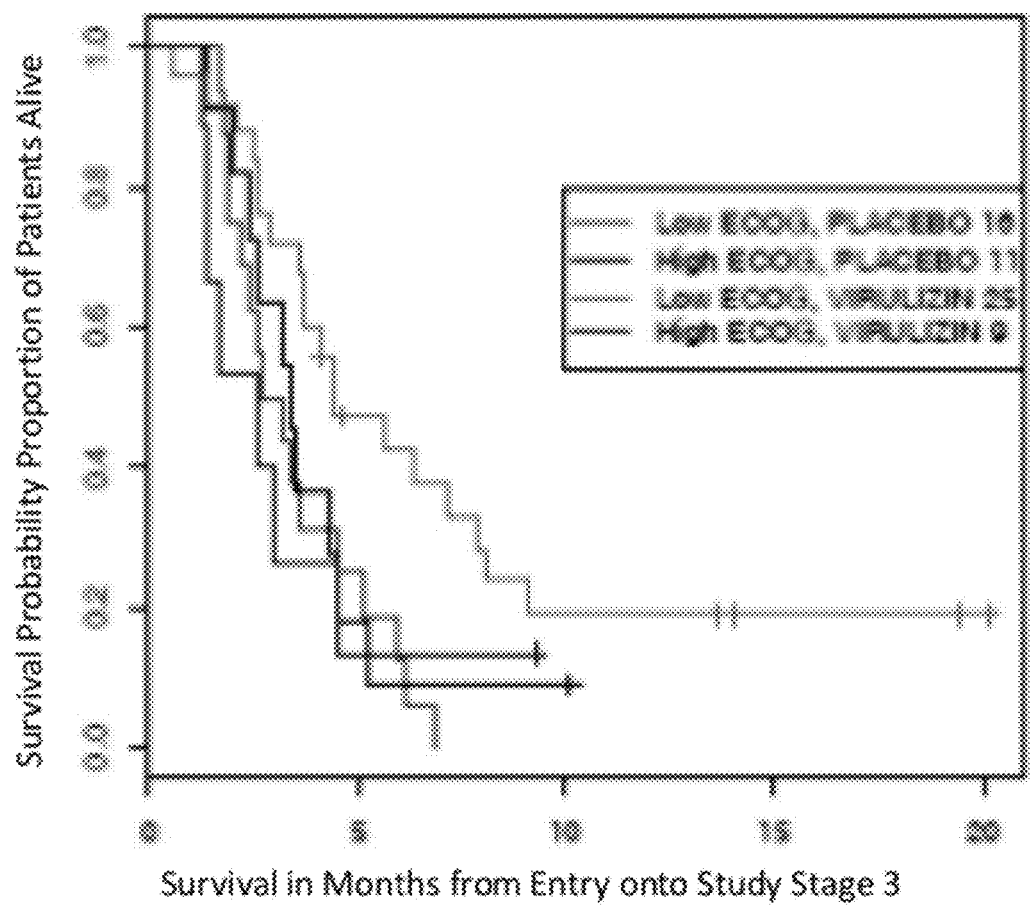
FIG. 13 is a graph comparing the Kaplan-Meier estimations of survival during study Stage 3 of the Intention to Treat population from the time of enrollment in study Stage 3 until death from any cause or censor from follow-up for the 61 patients who treated with 5-FU in study Stage 3.

In FIG. 13, patients were grouped by study treatment in Stage 3 (VIRULIZIN® plus 5-FU or placebo plus 5-FU) and by ECOG score, specifically Low ECOG score of 0 or 1 versus High ECOG score of 2 at study enrollment. During study Stages 1 and/or 2 these patients were treated with VIRULIZIN® plus gemcitabine (34 patients) or placebo plus gemcitabine (27 patients.) One plot is of Stage 3 survival of the 25 patients with Low ECOG score at study enrollment who were treated with VIRULIZIN® plus 5-FU in Stage 3 \who (median survival in Stage 3 of 4.4 months.) Another plot is of Stage 3 survival in Stage 3 of the 9 patients of High ECOG score at study enrollment were treated with VIRULIZIN® plus 5-FU in Stage 3 (median survival in stage 3 of 2.63 months.) Another plot is of the Stage 3 survival of the 16 patients of Low ECOG score at study enrollment who were treated with placebo plus 5-FU in Stage 3 (median survival in Stage 3 of 2.94 months.) Another plot is of the 11 patients of High ECOG score who were treated with placebo plus 5-FU (median survival in stage 3 of 3.43 months.) Patients participating in Stage 3 of the trial continued on the same test product assignment of either VIRULIZIN® or placebo as in study Stage 1 and/or 2. In study Stage 3 patients were treated with test product with or without 5-FU or only best supportive care.

Figure 14:
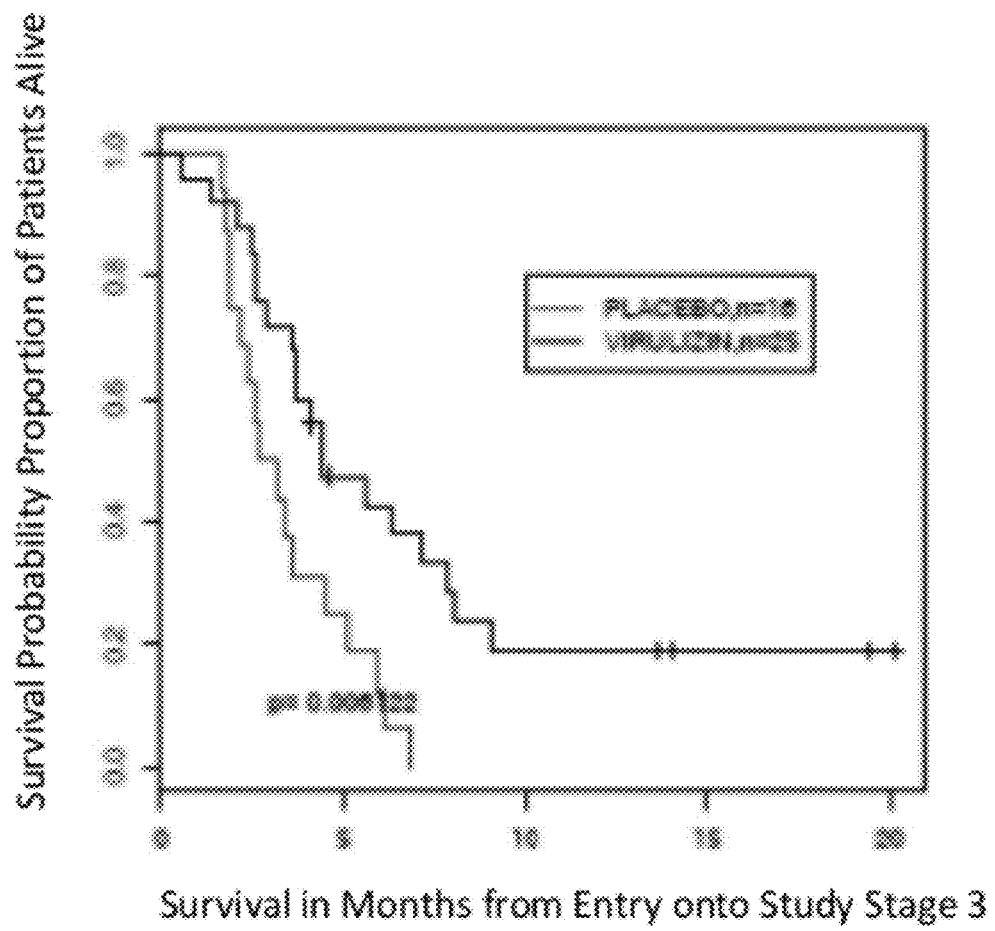
FIG. 14 is a graph comparing the Kaplan-Meier estimations of survival from the time of entry into study Stage 3 until death from any cause or censor from follow-up for all 41 patients in study Stage 3 of the Intention to Treat population with Low ECOG score of 0 or 1 at study enrollment who were treated with test product (either VIRULIZIN® or placebo) plus 5-FU during Stage 3.

In FIG. 14, one plot is of survival in study Stage 3 of the 25 patients with Low ECOG score at study enrollment who were treated with VIRULIZIN® plus 5-FU (median survival in Stage 3 of 4.4 months.) Another plot is of the survival in study Stage 3 of the 16 patients with Low ECOG score at study enrollment who were treated with placebo plus 5-FU median survival in Stage 3 of 2.94 months.) Statistical analysis of the median survival in Stage 3 of patients with Low ECOG score status who were treated with 5-FU plus VIRULIZIN® using survival in Stage 3 versus the survival in Stage 3 of the Low ECOG score patients treated with placebo plus 5-FU in Stage 3 indicated a very highly significant p-value of 0.000122). This indicates a highly statistically significant increase of 1.46 months in median survival of seen for the Low ECOG score patients treated with VIRULIZIN® plus 5-FU during Stage 3 (as salvage treatment after gemcitabine) versus the Low ECOG score patients treated with placebo plus 5-FU in Stage 3. This increase is also clinically significant, as a 1.5 months increased median survival (survival from study enrollment to death from any cause) for gemcitabine (median Overall Survival of 5.7 months) versus the median Overall Survival of 4.2 months for patients treated with 5-FU was key for the US FDA to support the marketing approval of gemcitabine for treatment of patients with advanced pancreatic cancer. In additional to increased survival during Stage 3, 4(16%) of the 25 patients with Low ECOG score who were treated with VIRULIZIN® plus 5-FU in Stage 3 were still alive and their survival data was censured at the end of the data collection period for the study. None (0%) of the 16 Low ECOG score patients treated with placebo plus 5-FU during Stage 3 were alive at the end of the study data collection period. Patients participating in Stage 3 of the trial continued on the same study drug assignment of either VIRULIZIN® or placebo as in study Stage 1 and/or 2. In study Stage 3 patients were treated with test product with or without 5-FU or only best supportive care.

CONCLUSIONS

Chemonaive patients with locally advanced or metastatic pancreatic cancer receiving VIRULIZIN® plus gemcitabine did not derive statistically significant benefit measured by survival from the time of study enrollment over those receiving placebo plus gemcitabine. However, there was a highly clinically and statistically significant survival benefit associated with VIRULIZIN® treatment after treatment with VIRULIZIN® plus gemcitabine measured by survival from the time of enrollment in Stage 3 of the study. Specifically, 4 of 25 (17%) patients having an ECOG score of 0 or 1 and that were treated with VIRULIZIN® and 5-FU in Stage 3 of the study were alive at the end of Stage 3 of the study and further survival data collection was censored. In contrast, every patient having an ECOG score of 0 or 1 that was treated with placebo and 5-FU in Stage 3 of the study was deceased by the end of the study.

Safety assessments demonstrated results that were not unexpected for a population with locally advanced or metastatic pancreatic cancer. Types, frequencies, intensity and causality of AEs were similar between the VIRULIZIN® plus gemcitabine group and the placebo plus gemcitabine group. Importantly, the addition of VIRULIZIN® to standard gemcitabine or 5-FU therapy regimens did not impart any observed new risks nor did it increase the frequency or severity of those risks normally associated with these treatments.

Example 2

Study Objectives

The primary efficacy objective is to compare the effects of a combination of VIRULIZIN® and 5-fluorouracil (5-FU) versus a combination of placebo and 5-FU on the overall survival of patients with unresectable or metastatic pancreatic cancer previously treated with a gemcitabine-based adjuvant or first-line therapy. Overall survival is defined as the time from study randomization to death from any cause. Secondary efficacy objectives are to compare the following parameters between the two treatment groups: the overall response rate (ORR) (the sum of complete response [CR] and partial response [PR] rates) based on the investigator's objective assessment of response; the time to disease progression based on investigator's objective assessment of response; the quality of life as determined by the Functional Assessment of Chronic Illness Therapy [FACIT] fatigue scale measured at screening and at the beginning of each cycle; the patient's pain, based on each patient's assessment of worst pain over the prior 24 hours using a 10-point pain scale on a weekly basis; and Eastern Cooperative Oncology Group (ECOG) score assessed by the physician at the beginning of each treatment cycle.

Secondary clinical pharmacology (pharmacokinetic and pharmacodynamic) objectives are planned to compare the following parameters between the two treatment groups: estimate 5-FU exposure from the first 24 patients randomized following their first and third infusions of 5-FU; and determination of the pharmacodynamic profile of VIRULIZIN® immune stimulation, especially enumeration of natural killer cells and cytotoxic monocytes, and quantification of cytokine plasma levels (IL-12, IL-17E, TNF-alpha) from approximately 80 patients at selected study centers.

Secondary safety objectives are to compare the following parameters between the two treatment groups: type, frequency, severity, and causality of all adverse events assessed according to the National Cancer Institute Common Toxicity Criteria (NCI-CTC) Version 4.0 at each study visit; serum chemistry panel assessed weekly throughout study treatment; complete blood count with platelets and differential assessed weekly throughout study treatment; vital sign measurements assessed at each study visit; physical examination findings at the beginning of each cycle; body weight at each study visit. (Weight gain or weight loss ≧10% from study baseline which does not improve for at least 4 weeks may be considered evidence of clinical progression at the investigator's discretion); and concomitant medication usage at each study visit.

Study Design

This planned Phase III randomized, double-blind, placebo-controlled, multi-center trial will include a screening period up to 14 days followed by dosing with 5-FU every week on 4-week treatment cycle plus either VIRULIZIN® or placebo. Treatment will continue until disease progression or other study-specified reasons; follow-up will continue until death.

Number of Patients

A total of 238 patients will be randomized in a 1:1 ratio to Arm A (VIRULIZIN® and 5-FU) or Arm B (placebo and 5-FU). Patients who enroll in the study but fail to receive study drug will be replaced.

Study Entry Criteria

Male and female patients aged 18 years or older with unresectable or metastatic pancreatic adenocarcinoma, who have had no prior fluoropyrimidine treatment but who have previously been treated with gemcitabine alone or in combination, who have an ECOG score of 0 or 1, and who meet all other eligibility criteria may be enrolled.

Test Product, Dose, Mode of Administration

Dose, route, frequency: 3 mL by intramuscular injection 3 times weekly, administered every other day for a total of 3 injections during each week of every 4-week treatment cycle.

Combination Therapy Product 5-fluorouracil (5-FU); Dose, route, frequency: 600 mg/m2 as a 30-minute infusion on the first day of each week of every 4-week treatment cycle.

Treatment Regimens

Arm A (VIRULIZIN® and 5-FU) or Arm B (placebo and 5-FU).

Criteria for Evaluation

Efficacy assessments include survival follow-ups; pain and analgesic usage; ECOG score; the FACIT-Fatigue scale; and investigator assessment of all measurable and non-measurable disease per Response Evaluation Criteria in Solid Tumors (RECIST) criteria. Pharmacokinetic assessments include estimated 5-FU exposure from the first 24 patients randomized following their first and third infusions of 5-FU. Pharmacodynamic assessments include markers of immune stimulation and cytokine plasma levels from approximately 80 patients at selected study centers. Safety assessments include the evaluation of serum chemistry, hematology, coagulation studies, urinalysis, vital signs, screening electrocardiograms, physical examinations, concomitant medication use, and AEs.

Sample Size Determination

Assuming an estimated 20% screen failure rate, approximately 286 patients will be screened to ensure 238 patients enrolled. Assuming the median survival times of VIRULIZIN® plus 5-FU and placebo plus 5-FU are 4.4 and 2.94 months, respectively (based on previous Phase III trial LOR/VIR/P03/002), 225 events (deaths) will provide 85% statistical power to detect a difference between survival times using a 2-sided log-rank test with a significance level of 0.05 in a 2-look clinical trial (calculated using East 5.3 by Cytel).

Study and Treatment Duration

The overall study duration is expected to be 26 months (17 months of active enrollment and 9 months of follow-up).

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology, which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

What is claimed is:

1. A method for treating a cancer, including the steps of:
   determining a patient to have an ECOG (Eastern Cooperative Oncology Group) score of 0 or 1 and selecting that patient for treatment; and
   administering to the patient an effective amount of an immunomodulating composition comprising small molecular weight components of less than 3000 daltons, and having the following properties:
   (i) is extracted from bile of animals;
   (ii) is capable of stimulating monocytes and/or macrophages;
   (iii) is capable of modulating tumor necrosis factor production and/or release;
   (iv) contains no measurable level of IL-1α, IL-1β, TNF, IL-6, IL-8, IL-4, GM-CSF or IFN-γ;
   (v) is not cytotoxic to human peripheral blood mononuclear cells; and
   (vi) is not an endotoxin.

2. The method of claim 1, wherein the immunomodulating composition is in a pharmaceutically acceptable carrier.

3. The method of claim 1, wherein said administering step is further defined as administering the immunomodulating composition in a dose of 3 mL three times weekly by intramuscular injection for as long as 24 months.

4. The method of claim 1, wherein the cancer is chosen from the group consisting of pancreatic cancer, malignant melanoma, breast cancer, cervical cancer, prostate cancer, ovarian cancer, endometrial cancer, lung cancer, Kaposi's sarcoma, leukemia, lymphoma, gastric cancer, colon cancer, colorectal cancer, esophageal cancer, renal cancer, and head and neck cancer.

5. The method of claim 1, wherein the patient has previously been administered gemcitabine and failed gemcitabine therapy.

6. The method of claim 1, wherein the patient's cancer has recurred or advanced after previous radiotherapy, surgical resection, or chemotherapy.

7. The method of claim 1, further including the step of administering an effective amount of at least one anticancer agent.

8. The method of claim 7, wherein said administering step is further defined as administering the anticancer agent in a method chosen from the group consisting of before the immunomodulating composition, simultaneously with the immunomodulating composition, and after the immunomodulating composition.

9. The method of claim 8, wherein the anticancer agent is chosen from the group consisting of a chemotherapeutic drug, radiation, a gene therapy agent, hormonal manipulation, immunotherapy, and an antisense oligonucleotide.

10. The method of claim 9, wherein the chemotherapeutic drug is chosen from the group consisting of gemcitabine, 5-fluorouracil, folinic acid, capecitabine, dacarbazine, taxol, taxotere, cisplatin, irinotecan, mitoxantrone, oxaliplatin, and combination therapies including one or more of these agents including gemcitabine.

11. The method of claim 9, wherein the chemotherapeutic drug is gemcitabine and is administered in a dose of an intravenous infusion of 1 g/m$^2$ weekly for the first 7 weeks, followed by a week of rest, and subsequently in 28-day cycles with gemcitabine dosing on days 1, 8 and 15.

12. The method of claim 9, wherein the chemotherapeutic drug is 5-fluorouracil and is administered intravenously at a dose of 600 mg/m$^2$ weekly.

13. The method of claim 9, wherein the chemotherapeutic drug is chosen from the group consisting of 5-fluorouracil administered intravenously in a dose of 300 to 2400 mg/m$^2$ weekly and capecitabine administered orally at a dose of 2500 mg/m$^2$ daily with food for 2 weeks followed by a 1-week rest period given as 3 week cycles.

14. The method of claim 8, wherein said step of administering an effective amount of at least one anticancer agent is further defined as administering gemcitabine during administration of the immunomodulating composition, and subsequently administering 5-fluorouracil during administration of the immunomodulating composition.

15. The method of claim 8, further including the step of administering a composition that treats adverse side effects of the anticancer agent.

16. The method of claim 1, further including the steps of the immunomodulating composition activating macrophages and enhancing cell-mediated immune response to tumors.

17. The method of claim 16, wherein said activating macrophages step is further defined as increasing expression of TNF-α.

18. The method of claim 16, wherein said enhancing step is further defined as increasing production and secretion of IL-17E by B cells resulting in expansion in number of and increased infiltration of eosinophils and natural killer (NK) cells into tumors.

* * * * *